United States Patent
Lee et al.

(10) Patent No.: US 9,062,088 B2
(45) Date of Patent: Jun. 23, 2015

(54) CDK-INHIBITING PYRROLOPYRIMIDINE CARBOXAMIDE DERIVATIVE OR PHARMACEUTICALLY ACCEPTABLE SALT THEREOF, AND PHARMACEUTICAL COMPOSITION CONTAINING THE SAME AS ACTIVE INGREDIENT FOR PREVENTING OR TREATING HEPATOCELLULAR CARCINOMA

(75) Inventors: Seung Ki Lee, Seoul (KR); Byeong Moon Kim, Seoul (KR); Seung Ju Cho, Gyeonggi-do (KR); Young Jong Kim, Seoul (KR)

(73) Assignee: SNU R&DB Foundation, Seoul (KR)

( * ) Notice: Subject to any disclaimer, the term of this patent is extended or adjusted under 35 U.S.C. 154(b) by 21 days.

(21) Appl. No.: 13/882,955

(22) PCT Filed: Nov. 2, 2010

(86) PCT No.: PCT/KR2010/007650
§ 371 (c)(1),
(2), (4) Date: May 31, 2013

(87) PCT Pub. No.: WO2012/060482
PCT Pub. Date: May 10, 2012

(65) Prior Publication Data
US 2013/0237495 A1 Sep. 12, 2013

(51) Int. Cl.
| A01N 43/04 | (2006.01) |
| C07H 19/16 | (2006.01) |
| A61K 31/70 | (2006.01) |
| C07H 19/14 | (2006.01) |
| A61K 31/7068 | (2006.01) |
| C07H 1/00 | (2006.01) |
| A61K 31/519 | (2006.01) |

(52) U.S. Cl.
CPC .......... *C07H 19/14* (2013.01); *A61K 31/7068* (2013.01); *C07H 1/00* (2013.01); *A61K 31/519* (2013.01)

(58) Field of Classification Search
CPC ... A61K 31/7068; A61K 31/519; C07H 1/00; C07H 19/14
See application file for complete search history.

(56) References Cited

U.S. PATENT DOCUMENTS

2002/0035077 A1 3/2002 Tam et al.
2009/0117651 A1 5/2009 Gartel et al.

OTHER PUBLICATIONS (R) Kim et al., "Selectivity Between N-1 and N-7 Nucleosides: Regioselective Synthesis of BMK-Y101, A Potent cdk7 and 9 Inhibitor," Tetrahedron Letters, 54(40), 5484-5488 (Aug. 2, 2013).*
Cho et al., "Xylocydine, a novel Cdk inhibitor, is an effective inducer of apoptosis in hepatocellular carcinoma cells in vitro and in vivo," *Cancer Letters* 287:196-206, 2010.
Ham et al., "Xylocydine, a Novel Inhibitor of Cyclin-Dependent Kinases, Prevents the Tumor Necrosis Factor-Related Apoptosis-Inducing Ligand-Induced Apoptotic Cell Death of SK-HEP-1 Cells," *The Journal of Pharmacology and Experimental Therapeutics* 308(3):814-819, 2004.
International Search Report from International Application No. PCT/KR2010/007650 dated Sep. 5, 2011 with an English-language translation.
Anderson et al., "Synthesis of tubercidin, 6-chlorotubercidin and related nucleosides," *Nucleosides & Nucleotides* 8(7):1201-1216, 1989 (Chemical Abstract Citation), Chem. Abstr., 112,23631a-23634a(1990);only Abstr. suppl.
Huang et al., "Synthesis and in vitro antitumor activity of some amino-deoxy 7-hexofuranosylpyrrolo[2,3-*d*] pyrimidines," *Carbohydrate Research* 308:319-328, 1998.

* cited by examiner

*Primary Examiner* — Lawrence E Crane
(74) *Attorney, Agent, or Firm* — Klarquist Sparkman, LLP

(57) ABSTRACT

The present invention relates to a CDK-inhibiting pyrrolopyrimidine carboxamide derivative or a pharmaceutically acceptable salt thereof, and a pharmaceutical composition comprising the same as an active ingredient for preventing or treating liver cell cancer. Compositions comprising a pyrrolopyrimidine carboxamide derivative of the present invention suppress the cell growth of SNU-354 cell, which is a liver cancer stem cell in humans, by inhibiting CDK1 and CDK2, and induces cell apoptosis of the cell by inhibiting CDK7 and CDK 7. Such compositions are useful for preventing or treating liver cell cancer.

11 Claims, 15 Drawing Sheets

CDK-INHIBITING PYRROLOPYRIMIDINE CARBOXAMIDE DERIVATIVE OR PHARMACEUTICALLY ACCEPTABLE SALT THEREOF, AND PHARMACEUTICAL COMPOSITION CONTAINING THE SAME AS ACTIVE INGREDIENT FOR PREVENTING OR TREATING HEPATOCELLULAR CARCINOMA

CROSS REFERENCE TO RELATED APPLICATIONS

This is the U.S. National Stage of International Application No. PCT/KR2010/007650, filed Nov. 2, 2010, which is incorporated herein by reference in its entirety.

BACKGROUND OF THE INVENTION

1. Field of the Invention

The present invention relates to a CDK-inhibiting pyrrolopyrimidine carboxamide derivative or a pharmaceutically acceptable salt thereof, and a pharmaceutical composition for preventing or treating hepatocellular carcinoma comprising the same as an active ingredient.

2. Description of the Related Art

Hepatocellular carcinoma (HCC) is the most lethal disease to the liver cirrhosis patients. Hepatocellular carcinoma demonstrates the 6th highest onset rate in the whole world and the death rate of it takes the third place among cancers. 1.3 out of 100,000 people caught this disease in USA between 1978~1980, which increased gradually to 3.3 people out of 100,000 between 1998~2001. The increase of the onset rate continues year after year. A few decades ago, hepatitis C virus (HCV) infection was believed to be the major cause. However, since hepatitis B virus (HBV) infection was more widely distributed world-widely than hepatitis C virus infection, it has been suspected that HBV infection might be the major reason of hepatocellular carcinoma. The onset rate of this disease is higher in Asia or Africa than in Western countries. It is still very hard to treat hepatocellular carcinoma because hepatocellular carcinoma demonstrates the expressions of various drug-resistant genes and hence the sensitivity to chemotherapy is very low. In hepatocellular carcinoma cases, the Cdk (cyclin dependent kinase) activity in tissues and cells is very high suggesting that the intracellular Cdk inhibitors (p16Ink4, p21Waf1, p27Kip1, etc) are suppressed or those subclones which form conjugates with Cdk have abnormal activities. Because of those, Cdk inhibitors can be an excellent candidate group for treating hepatocellular carcinoma. Among those inhibitors, flavopiridol and roscovitine have been clinically tested.

Intracellular Cdk inhibitors (p16Ink4, p21Waf1, p27Kip1, etc) are involved in important check points of cell cycle to play an important role in regulating cell cycle. According to the previous reports, the division in G1/S or G2/M check point in cell cycle leads to uncontrollable cell growth, resulting in cancer or apoptosis. Therefore, to understand the mechanism of Cdk inhibitors is very important in treating cancer.

Cdk regulates cell cycle progression and gene transcription, which are two necessary factors for the cancer cell growth. Cdk induces phosphorylations of important molecules for cell cycle such as Rb protein, etc, to regulate the entry of each stage of cell cycle. Cdk forms heterodimers with cyclins to form a new complex having noble activity. For example, Cdk2/cyclin E is being a necessary factor for the entry of S phage of cell cycle, and Cdk2/cycline A is being a necessary factor to be a bridge between S phase and G2 phase. Cdk induces phosphorylation of carboxyl-terminal domain of RNA polymerase II large subunit, by which it regulates gene transcription. Human RNA polymerase II carboxyl-terminal domain contains 52 repeats of heptapeptide (YSPTSPS) that is easily phosphorylated. It is known that diverse Cdks can induce phosphorylation of such part. Two most representative Cdk complexes are Cdk7/cyclin H/Mat1 that is a part of TFIIH complex inducing transcriptional initiation and Cdk9/cyclin T that is also called P-TEFb involved in transcriptional elongation.

The present inventors have studied to synthesize a novel Cdk inhibitor compound. As a result, the inventors succeeded in the synthesis of pyrrolopyrimidine carboxamide derivative and at last completed this invention by confirming that the said pyrrolopyrimidine carboxamide derivative had excellent Cdk inhibiting effect in in vitro test and in animal test to be effectively used for preventing or treating hepatocellular carcinoma.

SUMMARY OF THE INVENTION

It is an object of the present invention to provide a pyrrolopyrimidine carboxamide derivative or a pharmaceutically acceptable salt thereof.

It is another object of the present invention to provide a method for preparing the said pyrrolopyrimidine carboxamide derivative.

It is also an object of the present invention to provide a pharmaceutical composition for preventing or treating hepatocellular carcinoma that comprises the said pyrrolopyrimidine carboxamide derivative or a pharmaceutically acceptable salt thereof as an active ingredient.

To achieve the above object, the present invention provides a pyrrolopyrimidine carboxamide derivative represented by the following formula 1 or a pharmaceutically acceptable salt thereof.

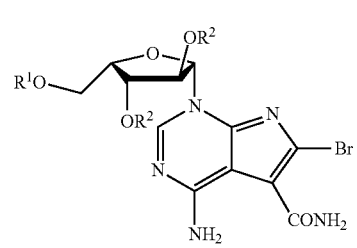

[Formula 1]

(In the Formula 1,
$R^1$ and $R^2$ are as defined in this description.)

The present invention also provides a method for preparing the said pyrrolopyrimidine carboxamide derivative.

In addition, the present invention provides a pharmaceutical composition for preventing or treating hepatocellular carcinoma that comprises the said pyrrolopyrimidine carboxamide derivative or a pharmaceutically acceptable salt thereof as an active ingredient.

ADVANTAGEOUS EFFECT

As explained hereinbefore, the composition containing the pyrrolopyrimidine carboxamide derivative of the present invention inhibits the growth of the human hepatocellular carcinoma cell line SNU-354 by inhibiting Cdk1 and Cdk2, and induces apoptosis of the human hepatocellular carcinoma cell line SNU-354 as a result of inhibiting Cdk7 and Cdk9. Therefore, the composition of the present invention can be effectively used for the prevention or treatment of hepatocellular carcinoma.

BRIEF DESCRIPTION OF THE DRAWINGS

The application of the preferred embodiments of the present invention is best understood with reference to the accompanying drawings, wherein.

SEQUENCE LISTING

Figure 1:
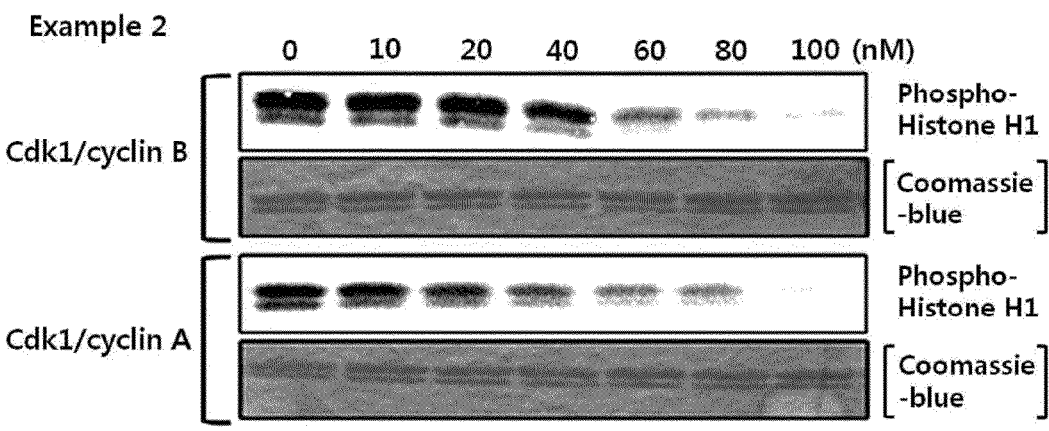
FIG. 1 is a diagram illustrating the result of electrophoresis examining the phosphorylations of Cdk1 and Cdk2 induced by the compound of an example of the present invention.

The Sequence Listing is submitted as an ASCII text file in the form of the file named Sequence_Listing.txt, which was created on Jan. 5, 2015, and is 2.26 KB, which is incorporated by reference herein.

DESCRIPTION OF THE PREFERRED EMBODIMENTS

Hereinafter, the present invention is described in detail.

The present invention provides a pyrrolopyrimidine carboxamide derivative represented by the following Formula 1 or a pharmaceutically acceptable salt thereof.

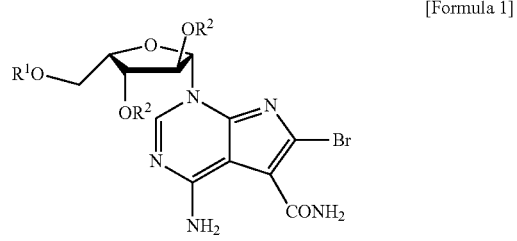

[Formula 1]

In the Formula 1,
$R^1$ is hydrogen or $R^3C(=O)$;
$R^3$ is $C_1$-$C_6$ straight or branched alkyl, $C_3$-$C_8$ cycloalkyl or phenyl;
$R^2$ is hydrogen or acetyl group.

More preferably, $R^3$ is methyl, ethyl, propyl, isopropyl, butyl, t-butyl, cyclopentyl, cyclohexyl or phenyl.

The compounds represented by the Formula 1 are as follows.

(1) 4-amino-6-bromo-1-((2S,3R,4R,5S)-3,4-dihydroxy-5-(hydroxymethyl)-tetrahydrofuran-2-yl)-1H-pyrrolo[2,3-d]pyrimidine-5-carboxamide;

(2) ((2S,3R,4R,5S)-5-(4-amino-6-bromo-5-carbamoyl-1H-pyrrolo[2,3-d]pyrimidine-1-yl)-3,4-dihydroxy-tetrahydrofuran-2-yl)methyl isobutyrate;
(3) ((2S,3R,4R,5S)-5-(4-amino-6-bromo-5-carbamoyl-1H-pyrrolo[2,3-d]pyrimidine-1-yl)-3,4-dihydroxy-tetrahydrofuran-2-yl)methyl pivalate;
(4) (2S,3R,4S,5S)-2-(4-amino-6-bromo-5-carbamoyl-1H-pyrrolo[2,3-d]pyrimidine-1-yl)-5-(isobutyryloxy methyl)-tetrahydrofuran-3,4-diyl diacetate;
(5) ((2S,3R,4R,5S)-5-(4-amino-6-bromo-5-carbamoyl-1H-pyrrolo[2,3-d]pyrimidine-1-yl)-3,4-dihydroxy-tetrahydrofuran-2-yl)methyl benzoate;
(6) ((2S,3R,4R,5S)-5-(4-amino-6-bromo-5-carbamoyl-1H-pyrrolo[2,3-d]pyrimidine-1-yl)-3,4-dihydroxy-tetrahydrofuran-2-yl)methyl propionate; and
(7) ((2S,3R,4R,5S)-5-(4-amino-6-bromo-5-carbamoyl-1H-pyrrolo[2,3-d]pyrimidine-1-yl)-3,4-dihydroxy-tetrahydrofuran-2-yl)methyl cyclohexanecarboxylate.

The pyrrolopyrimidine carboxamide derivative represented by Formula 1 of the present invention can be used as the form of a pharmaceutically acceptable salt, in which the salt is preferably acid addition salt formed by pharmaceutically acceptable free acids. Herein, the pharmaceutically acceptable salt indicates any organic or inorganic addition salt of the base compound represented by Formula 1 that is relatively nontoxic to a patient and has non-harmful activity whose side effect cannot reduce any positive effect of the said base compound represented by Formula 1. Whether it is inorganic or organic, a free acid can be used if it is pharmaceutically acceptable. Examples of the inorganic free acid include hydrochloric acid, bromic acid, nitric acid, sulfuric acid, perchloric acid, and phosphoric acid. Available organic free acids are exemplified by citric acid, acetic acid, lactic acid, malic acid, fumaric acid, gluconic acid, succinic acid, tartaric acid, galacturonic acid, embonic acid, glutamic acid, aspartic acid, oxalic acid, (D) or (L) malic acid, maleic acid, methanesulfonic acid, ethanesulfonic acid, 4-toluenesulfonic acid, salicylic acid, citric acid, benzoic acid, and malonic acid. The salt herein also includes alkali metal salts (sodium salt, potassium salt, etc) and alkali earth metal salts (calcium salt, magnesium salt, etc). For example, as acid addition salts, acetate, aspartate, benzate, besylate, bicarbonate/carbonate, bisulfate/sulfate, borate, camcilate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maliate, malonate, methylate, methylsulfate, naphthylate, 2-naphsilate, nicothinate, nitrate, orotate, oxalate, palmitate, pamotate, phosphate/hydrogen phosphate/dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, olamine, potassium, sodium, tromethamine, and zinc salt can be included. Among them, hydrochloride or trifluoroacetate is preferred.

The pyrrolopyrimidine carboxamide derivative represented by Formula 1 of the present invention not only includes a pharmaceutically acceptable salt but also any general salt, isomer, hydrate, and solvate.

The addition salt in this invention can be prepared by the conventional method known to those in the art. For example, the compound of Formula 1 is dissolved in water-miscible organic solvent such as acetone, methanol, ethanol, or acetonitrile, to which excessive organic acid or acid aqueous solution of inorganic acid is added to induce precipitation or crystallization. Then, the solvent or the excessive acid is evaporated from the mixture, followed by drying the mixture to give addition salt or suction-filtering the precipitated salt to give the same.

The present invention also provides a method for preparing a pyrrolopyrimidine carboxamide derivative comprising the following steps as shown in the following reaction formula 1:
preparing the compound of formula 4 by reacting the compound of formula 2 with the compound of formula 3 in the presence of trimethylsilyl trifluoromethanesulfonate (TMSOTf) after adding N,O-bis(trimethylsilyl)acetamide (BSA) to the compound of formula 2 (step 1);
preparing the compound of formula 5 by adding ammonium hydroxide solution to the compound of formula 4 (step 2); and
preparing the compound of formula 1a by adding hydrogen peroxide to the compound of formula 5 (step 3).

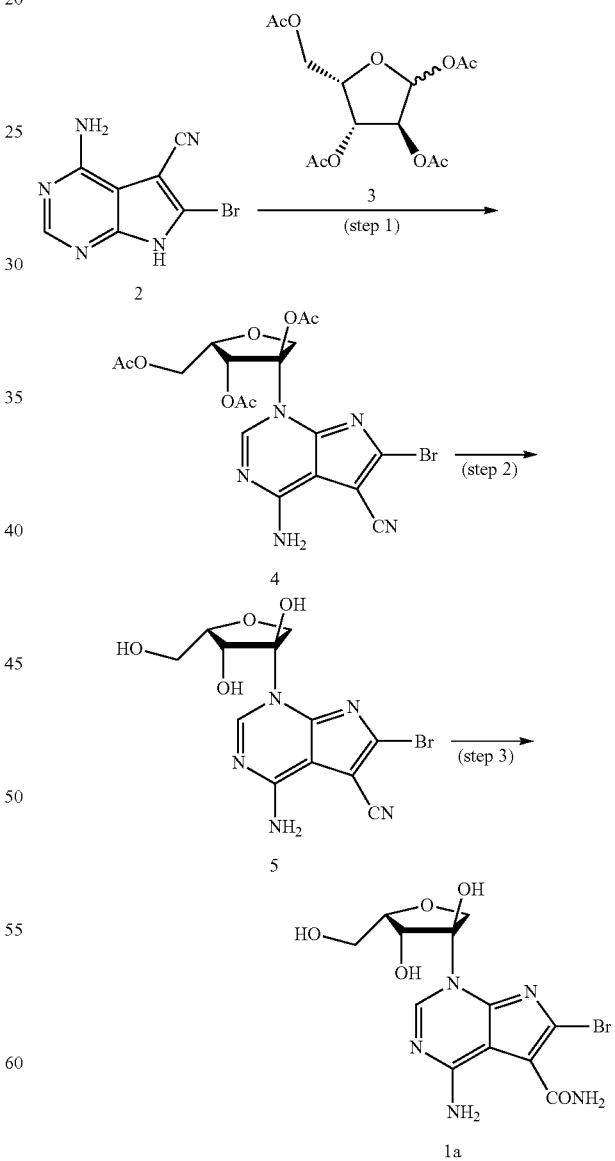

(In the reaction formula 1,
the formula 1a is included in the formula 1.)

Hereinafter, the method for preparing the pyrrolopyrimidine carboxamide derivative of the present invention is described in detail.

Step 1

In step 1, the compound of formula 2, the starting material, is reacted with N,O-bis(trimethylsilyl)acetamide (BSA) first in the presence of a solvent, which is then reacted with the compound of formula 3 to give the compound of formula 4.

This reaction is well-known to those in the field of organic chemistry. Reaction conditions for this reaction including reaction solvent, reaction temperature, and reaction time can be determined by considering reaction materials and reaction products, etc. For example, dichloroethane (DCE) and toluene were used as the reaction solvent in this invention and the reaction temperature was set at 80° C. to give the compound of formula 4.

Step 2

In step 2, the compound of formula 4 prepared in step 1 is reacted in the presence of a solvent to give the compound of formula 5.

Particularly, the compound of formula 4 is suspended in methanol, to which ammonia water is added at room temperature, followed by shaking to give the compound of formula 5.

Step 3

In step 3, another reaction is induced without separating the compound of formula 5 prepared in step 2 to give the compound of formula 1a.

Particularly, after confirming the generation of the compound of formula 5, hydrogen peroxide is added to the mixture, followed by shaking at room temperature for 8 hours to give the compound of formula 1a.

The method of the present invention can further include the additional step of preparing the compound of formula 1 via esterification with the compound of formula 1a (step 4), as shown in the following reaction formula 2.

Step 4

In step 4, the terminal primary hydroxy group of the compound of formula 1a is esterificated or the secondary hydroxy group thereof is protected to give the compound of formula 1.

Further, the compound of formula 2, which is the starting material, can be prepared by the following steps, as shown in the following reaction formula 3:

preparing the compound of formula 7 by adding hydrogenbromide to the compound of formula 6, tetracyanoethylene, in the presence of acetone and ethylacetate (step 1); and preparing the compound of formula 2 by adding triethyl orthoformate and ammonia water to the compound of formula 7 (step 2).

[Reaction Formula 3]

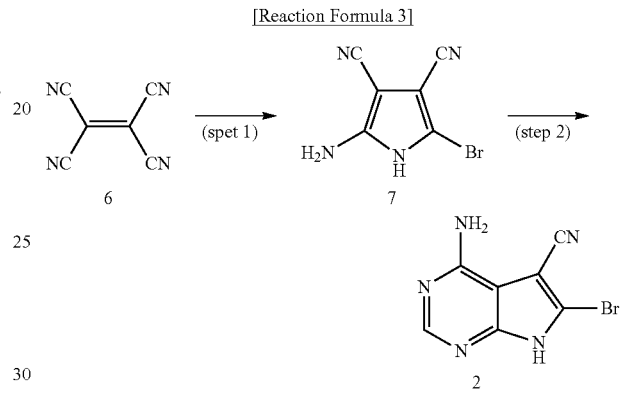

As shown in the following reaction formula 4, the compound of formula 3 presented in reaction formula 1 can be prepared as follows: L-xylose of formula 8 is reacted with boric acid, to which acetic acid and acetic anhydride are added, followed by reaction at high temperature.

[Reaction Formula 2]

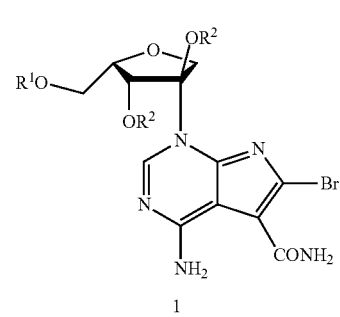

(In the reaction formula 2, $R^1$ and $R^2$ are as defined in formula 1 except eliminating H from $R^1$.)

[Reaction Formula 4]

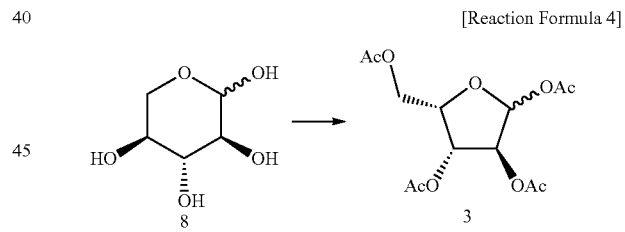

In addition, the present invention provides a pharmaceutical composition for preventing or treating hepatocellular carcinoma comprising the pyrrolopyrimidine carboxamide derivative represented by formula 1 or a pharmaceutically acceptable salt thereof as an active ingredient.

The said hepatocellular carcinoma indicates the cancer developed in hepatocytes. In general, liver cancer indicates hepatocellular carcinoma in large.

The said pyrrolopyrimidine carboxamide derivative or the pharmaceutically acceptable salt thereof in this invention has Cdk inhibiting activity, and at this time the said Cdk preferably includes Cdk1, Cdk2, Cdk7, and Cdk9.

The pyrrolopyrimidine carboxamide derivative of the present invention suppresses the growth of the human hepatocellular carcinoma cell line SNU-354 by inhibiting Cdk1 and Cdk2 and induces apoptosis of the human hepatocellular carcinoma cell line SNU-354 as a result of inhibiting Cdk7 and Cdk9, suggesting that it can be effectively used for preventing or treating hepatocellular carcinoma.

To be used as a medicinal composition, the pharmaceutical composition of the present invention comprising the pyrrolopyrimidine carboxamide derivative represented by formula 1 or a pharmaceutically acceptable salt thereof as an active ingredient can be prepared in many different formulations for oral or parenteral administration, but not always limited thereto.

The formulations for oral administration are exemplified by tablets, pills, hard/soft capsules, solutions, suspensions, emulsions, syrups, granules, and elixirs, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavors, and sweeteners can be additionally included therein.

The pharmaceutical composition comprising the pyrrolopyrimidine carboxamide derivative represented by formula 1 as an active ingredient of the present invention can be administered by parenterally and the parenteral administration includes subcutaneous injection, intravenous injection, intramuscular injection or intrathoracic injection.

To prepare the composition as a formulation for parenteral administration, the pyrrolopyrimidine carboxamide derivative represented by formula 1 or the pharmaceutically acceptable salt thereof is mixed with a stabilizer or a buffering agent to produce a solution or suspension, which is then formulated as ampoules or vials. The composition of the present invention can be sterilized and/or include an additive such as an antiseptic, a stabilizing agent, a wetting agent or an emulsifying agent, a salt for the regulation of osmotic pressure, and/or a buffer, and other therapeutically useful materials. The composition can be formulated by the conventional procedure including mixing, granulizing, or coating. The dose of the composition of the present invention for human can be determined by considering age, weight, and gender of a patient, administration pathway, health condition, and severity of disease, etc. For example, the effective dose for an adult patient in the body weight of 70 kg is preferably 0.1~1,000 mg/day, and more preferably 1~500 mg/day. The daily dose can be administered once a day or a few times a day according to the decision of a doctor or a pharmacist.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Preparation Example 1

Preparation of 4-amino-6-bromo-7H-pyrrolo[2,3-d]pyrimidine-5-carbonitrile) (4)

Step 1: Preparation of
2-amino-5-bromo-1H-pyrrole-3,4-dicarbonitrile) (3)

Tetracyanoethylene (10.02 g, 78.23 mmol) was dissolved in the mixed solvent of acetone (60 mL) and ethyl acetate (120 mL), to which hydrogen bromide (33 wt %, 60 mL) dissolved in acetic acid was added at 0~5° C. The yellow solid compound observed after one hour-stirring was isolated by filtering. After washing the compound with cold distilled water (100 mL), the mixture was dried in the air to give the target compound (11.02 g, 52.22 mmol, 66.8%).

$^1$H-NMR (500 MHz, DMSO-$d_6$, δH) 12.3 (br s, 1, N—H); 6.46 (br s, 2, NH$_2$).

mp>210° C.

Step 2: Preparation of 4-amino-6-bromo-7H-pyrrolo[2,3-d]pyrimidine-5-carbonitrile) (4)

The compound of formula 3 obtained in step 1 (10.57 g, 50.09 mmol) was suspended in distilled acetonitrile (170 mL). Triethyl orthoformate (20.0 mL, 182 mmol) was added thereto and the temperature was raised to the boiling point, followed by boiling for 4 hours. The obtained dark brown solution was cooled down at room temperature and the remaining debris were filtered out. Acetonitrile was eliminated by using vacuum to give 2-bromo-5-(ethoxymethylene) iminopyrrole-3,4-dicarbonitrile as a brown solid. The brown solid compound was dissolved in saturated ammonia water (100 mL) and the prepared solution was mixed with carbon (5.0 g) for destaining, which passed through a celite pad. This filtering process was repeated once again. To the filtered yellow solution was added acetic acid (80 mL) slowly until the white precipitate was generated. The suspension was stored at −5° C. for 8 hours and then filtered by using a filter. The filtered white solid compound was dried in a vacuum oven at 120° C. for 8 hours to give the target compound (9.99 g, 41.97 mmol, 84%).

$^1$H-NMR (500 MHz, DMSO-$d_6$, δH) 13.80 (bs, NH), 8.21 (s, H-2), 7.21 (bs, NH2).

$^{13}$C-NMR (125 MHz, DMSO-$d_6$, δC) 156.3, 150.4, 149.9, 125.3, 116.3, 104.0, 84.8.

HRMS (FAB+) Calcd for $C_7H_5BrN_5$ (M+) 237.9728. Found 237.9722.

Preparation Example 2

Preparation of
1,2,3,5-tetra-O-acetyl-L-xylofuranose) (5)

L-xylose of formula 10 (5.00 g, 33.3 mmol) and boric acid (4.53 g, 73.3 mmol) were dissolved in acetic acid (120 mL), followed by heating at 50° C. for 1 hour with stirring. Acetic anhydride (120 mL) was added thereto. The reaction mixture was heated at 50° C. for 3 days and then cooled down at room temperature, followed by extraction by using water (600 mL) and ethyl acetate (3×300 mL). The ethyl acetate extract was washed with saturated sodium_bicarbonate solution and brine, and moisture remained in the solvent was dried over magnesium sulfate. The extract was concentrated to give xylofuranose, the compound of formula 5, as a syrup (10.45 g, 32.8 mmol, 99%, α:β=1:1.8).

$^1$H NMR (500 MHz, CDCl$_3$, δH) 6.42 (d, 0.35H, J 4.6 Hz), 6.10 (s, 0.65H), 5.52 (dd, 0.35H, J 6.5, 6.5 Hz), 5.36 (dd, 0.65H, J 1.7, 5.6 Hz), 5.30 (dd, 0.35H, J 4.6, 6.2 Hz), 5.20 (d, 0.65H, J 1.0 Hz), 4.67-4.60 (m, 1H), 4.27-4.18 (m, 1.65H), 4.12 (dd, 0.35H, J 4.2, 12.2 Hz), 2.12 (s, 2H), 2.11 (s, 2H), 2.09 (s, 3H), 2.07 (s, 3H), 2.06 (s, 2H).

$^{13}$C NMR (125 MHz, CDCl$_3$, δC) 170.5, 170.3, 169.6, 169.5, 169.3, 169.2, 169.1, 98.8, 92.8, 79.9, 79.4, 75.3, 75.3, 74.3, 73.8, 62.3, 61.6, 21.0, 20.9, 20.8, 20.7, 20.6, 20.5, 20.4.

HRMS (ESI) calcd for (M+Na) $C_{13}H_{18}O_9$: 341.0843. found 341.0845.

Example 1

Preparation of 4-amino-6-bromo-1-((2S,3R,4R,5S)-3,4-dihydroxy-5-(hydroxymethyl)-tetrahydrofuran-2-yl)-1H-pyrrolo[2,3-d]pyrimidine-5-carboxamide) (1a)

Step 1: Preparation of (2S,3R,4S,5S)-2-(acetoxymethyl)-5-(4-amino-6-bromo-5-cyano-7H-pyrrolo[2,3-d]pyrimidin-1-yl)tetrahydrofuran-3,4-diyl diacetate) (6)

The compound of formula 2 (552 mg, 2.3 mmol) obtained in Preparation Example 1 was suspended in distilled dichloroethane (DCE) (23 mL), to which N,O-bis(trimethylsilyl)acetamide (BSA) (1.2 mL, 3.1 mmol) was added, followed by heating at 80° C. for 1 hour. When the suspension got clear, the solvent was eliminated by using vacuum. The obtained material was dissolved in distilled toluene (5 mL). To the solution were added tetra-O-acetyl-β-d-xylofuranose (382 mg, 1.2 mmol) of formula 3 dissolved in toluene and trimethylsilyl trifluoromethanesulfonate (TMSOTf) (0.24 mL, 289 mg, 1.3 mmol), followed by heating at 80° C. for about an hour. Upon completion of the reaction, the mixture was cooled down at room temperature, to which water (50 mL) was added. Organic material was extracted by using ethyl acetate, and the extract was washed with saturated sodium_bicarbonate solution and brine. The remaining moisture was dried over sodium sulfate and the solvent was also eliminated from the organic extracts. Column chromatography was performed to give the target compound as a yellow solid (1.087 g, 2.2 mmol, 94%).

$^1$H NMR (500 MHz, CDCl$_3$, δH) 8.46 (s, 1H), 6.54 (d, 1H), 6.14 (s, 2H), 5.50 (m, 1H), 5.44 (m, 1H), 4.72 (m, 1H), 4.40-4.50 (m, 2H), 2.21 (s, 3H), 2.13 (s, 3H), 2.04 (s, 3H).

$^{13}$C NMR (125 MHz, CDCl$_3$, δC) 170.6, 169.0, 155.0, 145.75, 140.6, 134.6, 116.3, 106.1, 91.1, 85.3, 80.5, 79.7, 74.2, 61.0, 21.0, 20.9, 20.7.

Step 2 and step 3: Preparation of 4-amino-6-bromo-1-((2S,3S,4S,5S)-3,4-dihydroxy-5-(hydroxymethyl)tetrahydrofuran-2-yl)-1H-pyrrolo[2,3-d]pyrimidine-5-carboxamide) (1a)

Step 2

The compound of formula 4 (3.183 g, 6.41 mmol) obtained in step 1 was suspended in methanol, to which saturated ammonium hydroxide solution was added, followed by stirring for 30 minutes. The reaction was observed via thin layer chromatography (TLC) and the generation of the compound of formula 5 was confirmed by the disappearance of the starting material.

$^1$H NMR (500 MHz, DMSO-d$_6$, δH) 8.44 (s, 1H), 6.06 (s, 1H), 6.00 (dd, 1H), 5.42 (m, 1H), 4.85 (m, 1H), 4.29 (d, 1H), 4.24 (d, 1H), 3.95 (s, 1H), 3.77 (m, 2H).

Step 3

After the disappearance of the starting material, 30% hydrogen peroxide solution was added thereto slowly, followed by stirring for 8 hours. Then, the solvent was eliminated by using vacuum. The compound was isolated via column chromatography, and then dissolved in hot water, which was stored at 4° C. for 4 hours. The generated precipitate was filtered by using a filter and vacuum-dried to give the compound of formula 1a as yellow powders (1.421 g, 3.66 mmol, 57%).

$^1$H NMR (500 MHz, DMSO-d$_6$, δH) 9.98 (d, 1H), 8.40 (s, 1H), 8.26 (d, 1H), 7.65 (bs, 1H), 7.11 (bs, 1H), 6.03 (s, 1H), 5.97 (s, 1H), 5.70 (s, 1H), 4.88 (t, 1H), 4.25 (m, 2H) 3.97 (s, 1H), 3.73-3.81 (m, 2H).

HRMS (FAB) calcd for (M+H) $C_{12}H_{15}BrN_5O_5$: 388.0257. found 388.0262.

Example 2

Preparation of ((2S,3R,4R,5S)-5-(4-amino-6-bromo-5-carbamoyl-1H-pyrrolo[2,3-d]pyrimidin-1-yl)-3,4-dihydroxy-tetrahydrofuran-2-yl)methyl isobutyrate) (1b)

The compound of formula 1a (452 mg, 1.16 mmol) obtained in step 3 of Example 1 was dissolved in pyridine (5.8 mL) and then temperature was lowered to −40° C. Isobutyryl anhydride (193 µl, 1.16 mmol) was added to the above solution slowly by using a syringe pump for 1 hour. The reaction mixture was stirred at −40° C. for 6 hours and then the temperature was raised to room temperature, followed by extraction with water (20 mL) and ethyl acetate (20 mL) three times. The ethyl acetate extract was washed with saturated sodium_bicarbonate solution and brine and then dried over magnesium sulfate, followed by concentration. Flash chromatography was performed to give the target compound of formula 1b (215 mg, 0.47 mmol, 40%).

$^1$H NMR (500 MHz, CDCl$_3$, δH) 10.54 (d, 1H), 8.15 (s, 1H), 7.16 (bs, 1H), 6.07 (d, 1H), 5.73 (s, 1H), 5.64 (bs, 1H), 4.79 (s, 1H), 4.64 (m, 1H), 4.50 (m, 1H), 4.41 (s, 1H) 4.31 (m, 1H), 4.27 (s, 1H), 2.59 (q, 1H), 1.17 (m, 6H).

Example 3

Preparation of ((2S,3R,4R,5S)-5-(4-amino-6-bromo-5-carbamoyl-1H-pyrrolo[2,3-d]pyrimidin-1-yl)-3,4-dihydroxy-tetrahydrofuran-2-yl)methyl pivalate) (1c)

Pivaloyl chloride (130 µl, 1.06 mmol) was dissolved in dimethylformamide (3 mL), to which imidazole (158 mg, 2.32 mmol) was added at 0° C., followed by stirring for 2 hours at 0° C. The compound of formula 1b (410 mg, 1.06 mmol) obtained in Example 1 dissolved in pyridine (2 mL) was slowly added thereto. The reaction mixture was stirred at 0° C. for 6 hours and then the temperature was raised to room temperature, followed by extraction with water (20 mL) and ethyl acetate (20 mL) three times. The ethyl acetate extract was washed with saturated sodium_bicarbonate solution and brine and then dried over magnesium sulfate, followed by concentration. Flash chromatography was performed to give the target compound (168 mg, 0.38 mmol, 35.8%).

$^1$H NMR (500 MHz, CDCl$_3$, δH) 9.98 (d, 1H), 8.41 (s, 1H), 8.27 (d, 1H), 7.65 (s, 1H), 7.10 (s, 1H), 6.05 (m, 2H), 5.95 (d, 1H), 4.40 (m, 3H), 4.30 (d, 1H), 4.01 (m, 1H) 1.15 (s, 9H).

Example 4

Preparation of (2S,3S,4R,5S)-2-(4-amino-6-bromo-5-carbamoyl-1H-pyrrolo[2,3-d]pyrimidin-1-yl)-5-(isobutyryloxymethyl)tetrahydrofuran-3,4-diyl diacetate) (1d)

The compound of formula 1b (257 mg, 0.56 mmol) obtained by the method performed as described in step 1 and step 2 of Example 1 was dissolved in pyridine (3 mL), to which acetic anhydride (317 μl, 3.36 mmol) was added. The reaction mixture was stirred at 40° C. for 6 hours, followed by extraction with water (10 mL) and ethyl acetate (3×10 mL). The ethyl acetate extract was washed with saturated sodium_bicarbonate solution and brine and then dried over magnesium sulfate, followed by concentration. Flash chromatography was performed to give the target compound (247 mg, 0.45 mmol, 81%).

$^1$H NMR (500 MHz, CDCl$_3$, δH) 10.47 (s, 1H), 8.34 (d, 1H), 6.55 (s, 1H), 6.02 (d, 1H), 5.65 (s, 1H), 5.49 (d, 1H), 5.43 (m, 1H), 4.73 (m, 1H), 4.41 (m, 2H), 2.51 (m, H) 2.21 (d, 3H), 2.12 (d, 3H), 1.13 (m, 3H), 1.08 (m, 3H).

Example 5

Preparation of ((2S,3S,4S,5S)-5-(4-amino-6-bromo-5-carbamoyl-7H-pyrrolo[2,3-d]pyrimidin-7-yl)-3,4-dihydroxytetrahydrofuran-2-yl)methyl benzoate) (1e)

Benzoyl chloride (232 μl, 2.01 mmol) was dissolved in dimethylformamide (2 mL), to which imidazole (280 mg, 4.02 mmol) was added at 0° C., followed by stirring for 2 hours at 0° C. The compound of formula 1a (410 mg, 1.00 mmol) obtained in Example 1 dissolved in pyridine (2 mL) was slowly added thereto. The reaction mixture was heated at 40° C. for hours and then cooled down at room temperature. The progress of the reaction was observed by HPLC. Upon completion of the reaction, extraction was performed with water (20 mL) and ethyl acetate (3×20 mL). The ethyl acetate extract was washed with saturated sodium bicarbonate solution and brine and then dried over magnesium sulfate, followed by concentration. Flash chromatography was performed to give the target compound (192 mg, 0.39 mmol).

$^1$H NMR (500 MHz, Acetonitrile-d$_3$, δH) 10.36 (s, 1H), 8.34 (s, 1H), 8.01 (d, 2H), 7.65 (m, 1H), 7.51 (m, 2H), 7.08 (s, 1H), 6.74 (s, 1H), 6.20 (s, 1H), 6.06 (d, 1H), 5.83 (s, 1H) 4.73 (m, 1H), 4.64 (m, 3H), 4.31 (s, 1H), 4.24 (d, 1H).

Example 6

Preparation of ((2S,3S,4S,5S)-5-(4-amino-6-bromo-5-carbamoyl-7H-pyrrolo[2,3-d]pyrimidin-7-yl)-3,4-dihydroxytetrahydrofuran-2-yl)methyl propionate) (1f)

Propionic acid (83 μl, 1.10 mmol) was dissolved in pyridine (3 mL), to which carbonyldiimidazole (178 mg, 1.10 mmol) was added slowly at 0° C. The mixture was stirred at 0° C. for 1.5 hour, which was slowly added to the pyridine (2 mL) solution containing the compound of formula 1a (388 mg, 1.00 mmol) obtained in Example 1 dissolved therein. The progress of the reaction was observed by HPLC. Upon completion of the reaction, extraction was performed with water (20 mL) and ethyl acetate (3×20 mL). The ethyl acetate extract was washed with saturated sodium bicarbonate solution and brine and then dried over magnesium sulfate, followed by concentration. Flash chromatography was performed to give the target compound (178 mg, 0.40 mmol).

$^1$H NMR (500 MHz, DMSO-d$_6$, δH) 9.98 (d, 1H), 8.42 (s, 1H), 8.28 (d, 1H), 7.64 (s, 1H), 7.11 (s, 1H), 6.08 (d, 1H), 6.04 (s, 1H), 5.98 (d, 1H), 4.41 (m, 3H), 4.31 (d, 1H), 4.03 (dd, 1H), 2.35 (m, 2H), 1.04 (t, 3H).

Example 7

Preparation of ((2S,3S,4S,5S)-5-(4-amino-6-bromo-5-carbamoyl-7H-pyrrolo[2,3-d]pyrimidin-7-yl)-3,4-dihydroxytetrahydrofuran-2-yl)methyl cyclohexanecarboxylate) (1g)

Cyclohexanecarboxylic acid chloride (136 μl, 1.06 mmol) was dissolved in dimethylformamide (1 mL), to which imidazole (150 mg, 2.20 mmol) was added at 0° C., followed by stirring for 2 hours at 0° C. The compound of formula 1a (388 mg, 1.00 mmol) obtained in Example 1 dissolved in pyridine (5 mL) was slowly added thereto. The reaction mixture was stirred at 0° C. for 6 hours and then the temperature was raised to room temperature, followed by extraction with water (20 mL) and ethyl acetate (20 mL) three times. The ethyl acetate extract was washed with saturated sodium_bicarbonate solution and brine and then dried over magnesium sulfate, followed by concentration. Flash chromatography was performed to give the target compound (184 mg, 0.37 mmol, 37%).

$^1$H NMR (500 MHz, DMSO-d$_6$, δH) 9.98 (d, 1H), 8.42 (s, 1H), 8.27 (d, 1H), 7.64 (s, 1H), 7.11 (s, 1H), 6.08 (d, 1H), 6.04 (s, 1H), 5.99 (m, 1H), 4.40 (m, 2H), 4.32 (d, 1H), 4.02 (td, 1H), 1.25-1.82 (m, 10H).

Experimental Example 1

In Vitro Kinase Inhibiting Activity Assay

<1-1> Cell Culture

The human hepatocellular carcinoma cell line SNU-354 was purchased from The Center for Functional Analysis of Human Genome, KOREA, and the conventional Cdk inhibitors olomoucine and roscosvitine were purchased from Calbiochem (San Diego, Calif., USA), which were then dissolved in DMSO at the concentration of 50 mM and stored at −20° C.

SNU-354 cells were cultured in RPMI 1640 (Invitrogen, CA, USA) supplemented with 10% FBS (Invitrogen) and antibiotics/antimycotics (Invitrogen) in a 5% CO$_2$ incubator at 37° C. Iso-pyrrolopyrimidine carboxamide was treated to the SNU-354 cells at the concentration of 10~50 μM for 24 hours.

<1-2> Measurement of Cdk1 and Cdk2 Inhibiting Activity

The following experiments were performed to investigate whether or not the compound of the present invention could inhibit Cdk1 and Cdk2 activities.

<1-2-1> In Vitro Kinase Activity Assay

Figure 2:
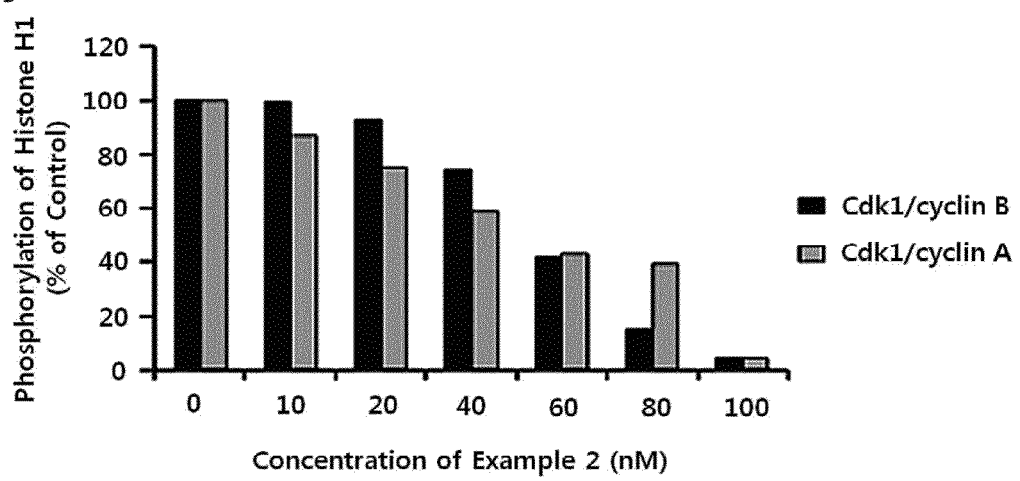
FIG. 2 is a graph illustrating the quantification of the result of electrophoresis examining the phosphorylations of Cdk1 and Cdk2 induced by the compound of an example of the present invention.

To kinase assay buffer (50 mM Tris (pH 7.4), 10 mM magnesium chloride, 1 mM EGTA, 40 mM β-glycerophosphate, 0.1 mM Na$_3$VO$_4$, 1 mM DTT, 0.1 μg/mL leupeptin, 0.1 μg/mL pepstatin A, 0.1 μg/mL antipain and 1 mM phenylmethylsulfonyl fluoride) were added 5 μg histone H1 as a substrate, 20 ng Cdk1/cyclin B or 40 ng Cdk2/cyclin A recombinant protein (Upstate, NY, USA) as an enzyme, 2.5 μCi [γ-32P]ATP, and 100 μM MgAc/ATP. The total reaction volume was adjusted to 50 μl. The compound of Example 2 was added to the reaction mixture, followed by inducing kinase reaction at 30° C. for 20 minutes. Upon completion of the reaction, the reaction mixture proceeded to electrophoresis on 12% SDS-polyacrylamide gel. Phosphorylation levels of Cdk1 and Cdk2 over the concentrations of the compound of Example 2 were confirmed by autoradiography, and the results are shown in FIG. 1, FIG. 2, and Table 1.

The intensity of bands was analyzed by densitometry (GS-800, Bio-Rad).

TABLE 1

| Example | Conc. (nM) | Phosphorylation (%) | |
| --- | --- | --- | --- |
| | | Cdk1 | Cdk2 |
| Example 2 | 0 | 100 | 100 |
| | 10 | 99.4 | 86.5 |
| | 20 | 92.2 | 75.0 |
| | 40 | 74.1 | 59.0 |
| | 50 | 50 | 50 |
| | 60 | 41.6 | 43.0 |
| | 80 | 15.3 | 39.2 |
| | 100 | 4.3 | 4.5 |

As shown in FIG. 1, FIG. 2, and Table 1, the phosphorylation level of Cdk1 or Cdk2 according to the treatment of the compound of Example 2 at the concentration of 0 nM was considered as 100%. When the compound of Example 2 was treated at the concentration of 10 nM, the phosphorylation level of Ckd1 histone H1 was 100%, which was consistent with the phosphorylation level when the compound was treated at the concentration of 0 nM. However, the phosphorylation level of Cdk2 histone H1 was reduced to 86.5%. When the compound was treated at the concentration of 20 nM, the phosphorylation levels of Cdk1 and Cdk2 histone H1 were reduced to 92.2% and 75.0% respectively. When the concentration of the compound of Example 2 was raised to 40~100 nM, the phosphorylation level of Cdk1 histone H1 was reduced to 74.1%~4.3%, while the phosphorylation level of Cdk2 histone H1 was reduced to 59.0%~4.5%. The above results indicate that the phosphorylations of Cdk1 and Cdk2 are inhibited by the compound of Example 2 dose-dependently. At that time, $IC_{50}$ of the compound to Cdk1 and Cdk2 was respectively 50 nM. Therefore, it was confirmed that the compound of the present invention could inhibit Cdk1 and Cdk2 activities significantly.

<1-2-2> Western Blotting

Figure 3:
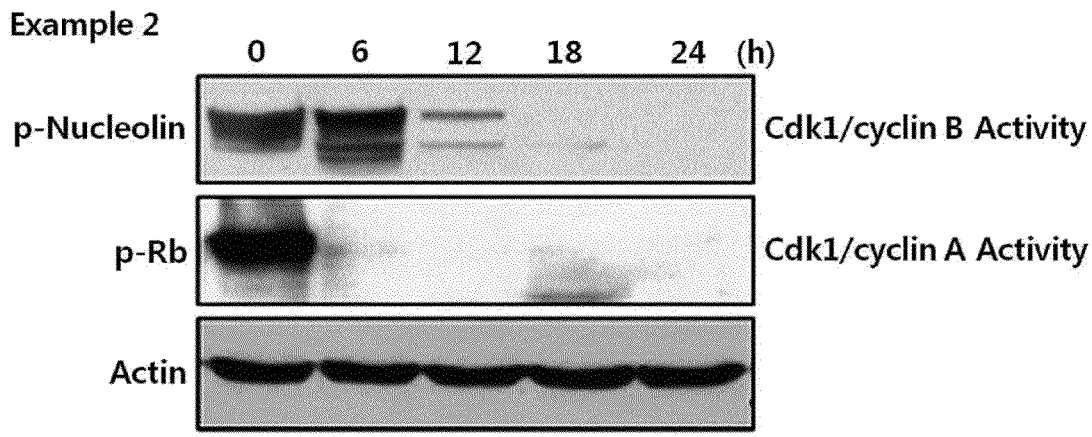
FIG. 3 is a diagram illustrating the result of Western blotting examining the Cdk1 phosphorylation over p-nucleolin and Cdk2 phosphorylation over p-Rb according to the treatment of the compound of an example of the present invention.
Figure 4:
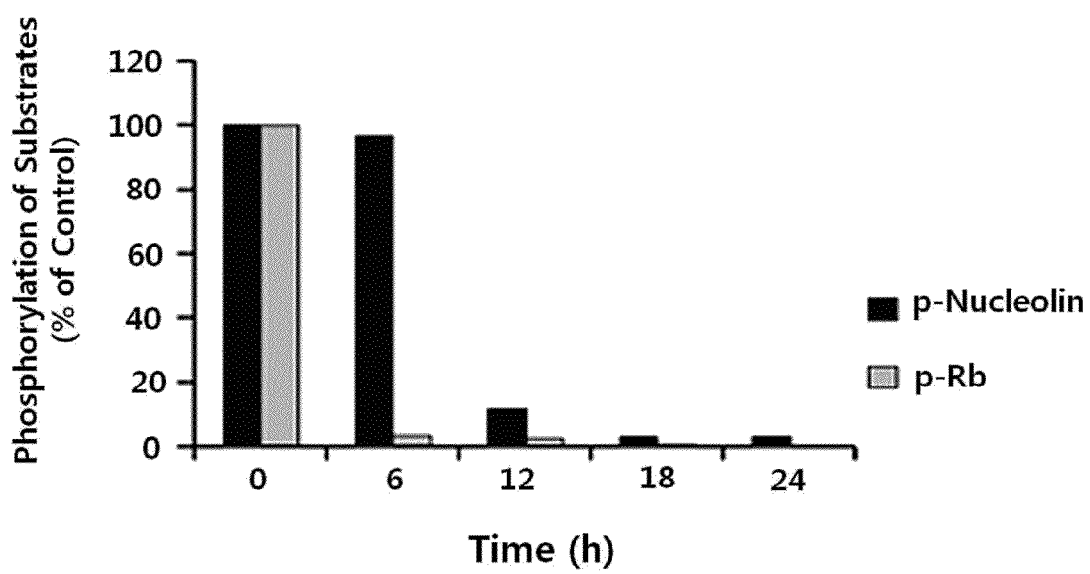
FIG. 4 is a graph illustrating the quantification of the result of Western blotting examining the Cdk1 phosphorylation over p-nucleolin and Cdk2 phosphorylation over p-Rb according to the treatment of the compound of an example of the present invention.
Figure 5:
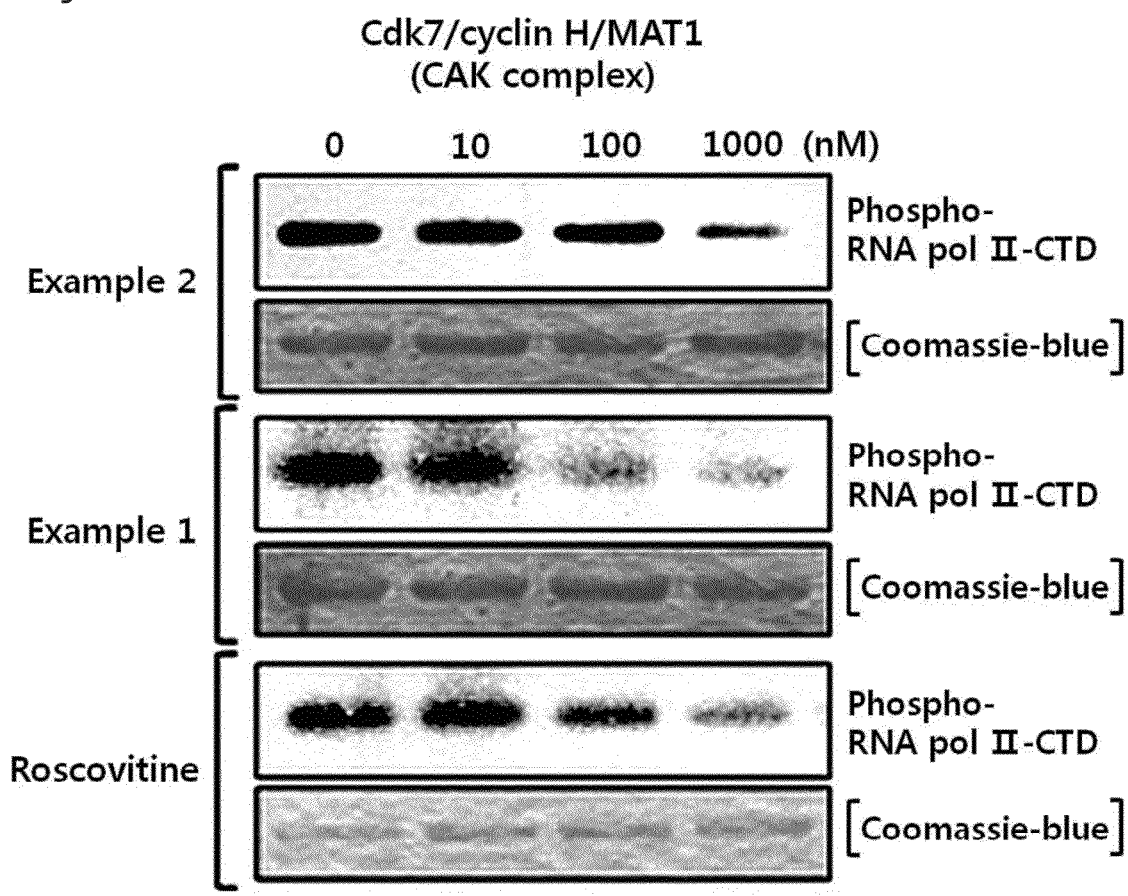
FIG. 5 is a diagram illustrating the result of electrophoresis analyzing the Cdk7 activity induced by the compound of an example of the present invention.
Figure 6:
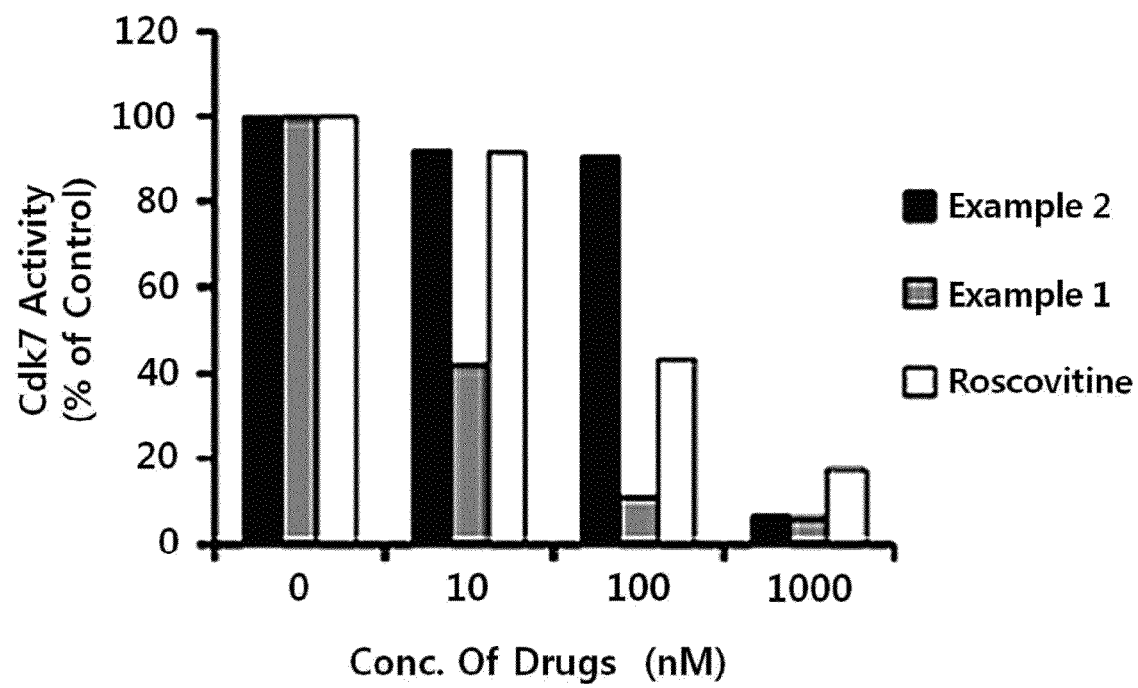
FIG. 6 is a graph illustrating the quantification of the result of electrophoresis analyzing the Cdk7 activity induced by the compound of an example of the present invention.
Figure 7:
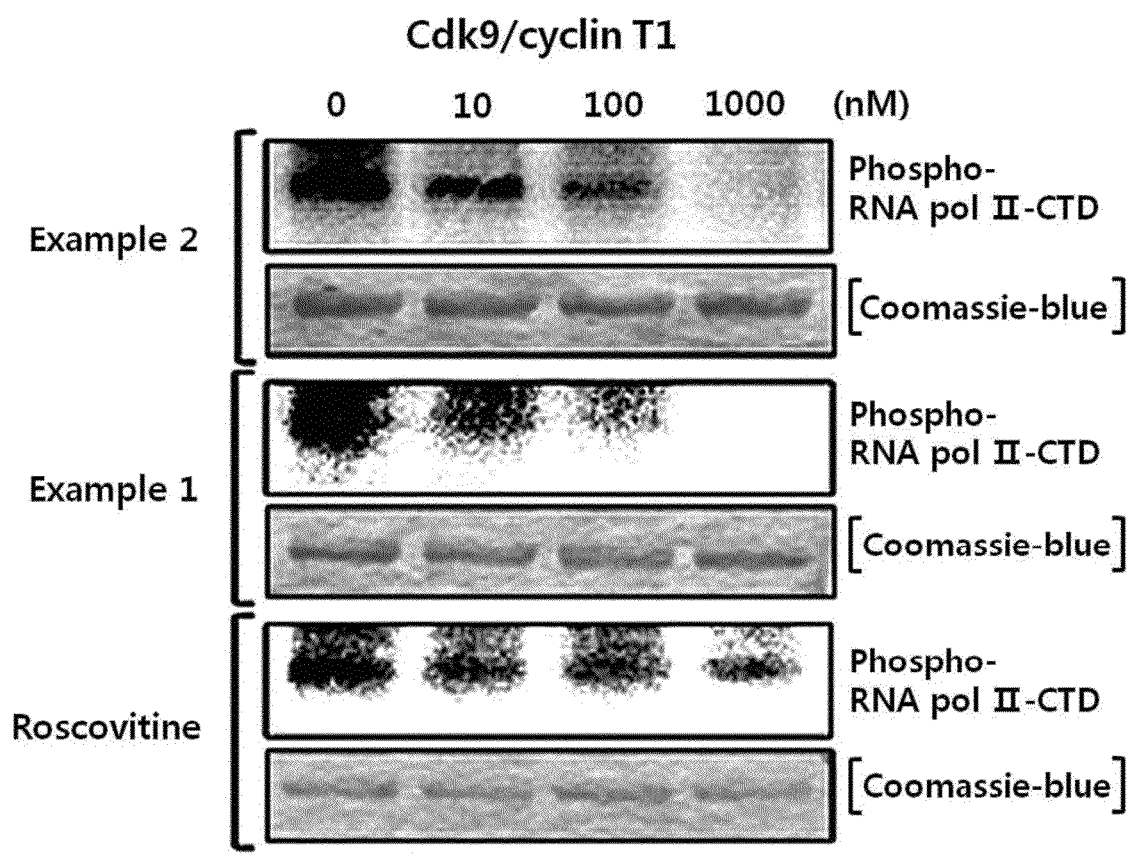
FIG. 7 is a diagram illustrating the result of electrophoresis analyzing the Cdk9 activity induced by the compound of an example of the present invention.
Figure 8:
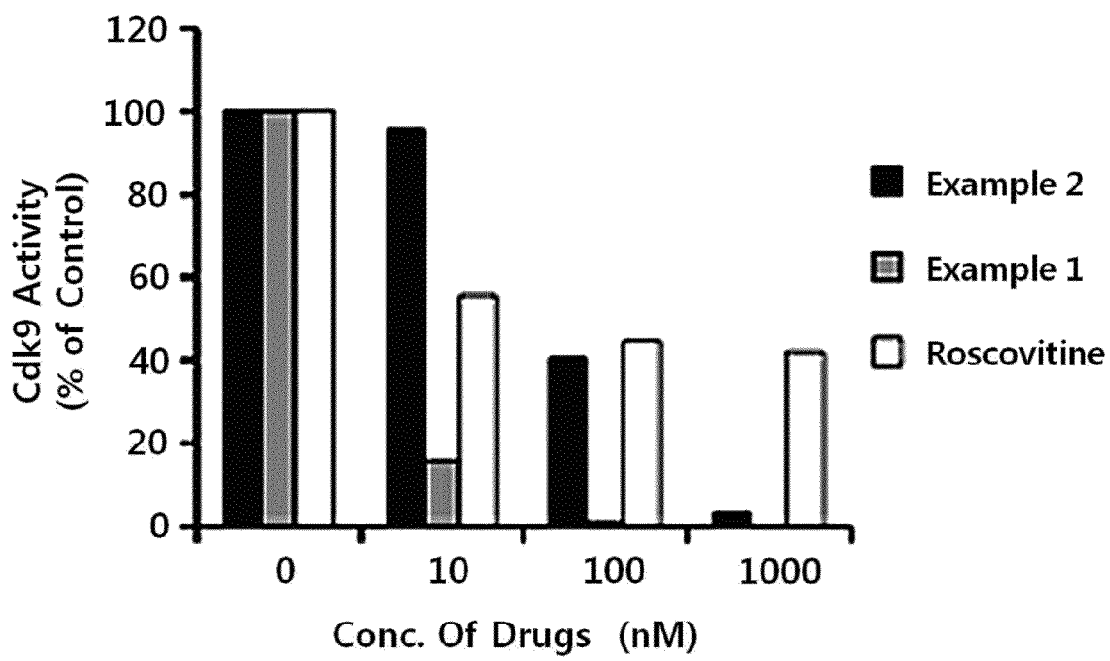
FIG. 8 is a graph illustrating the quantification of the result of electrophoresis analyzing the Cdk9 activity induced by the compound of an example of the present invention.
Figure 9:
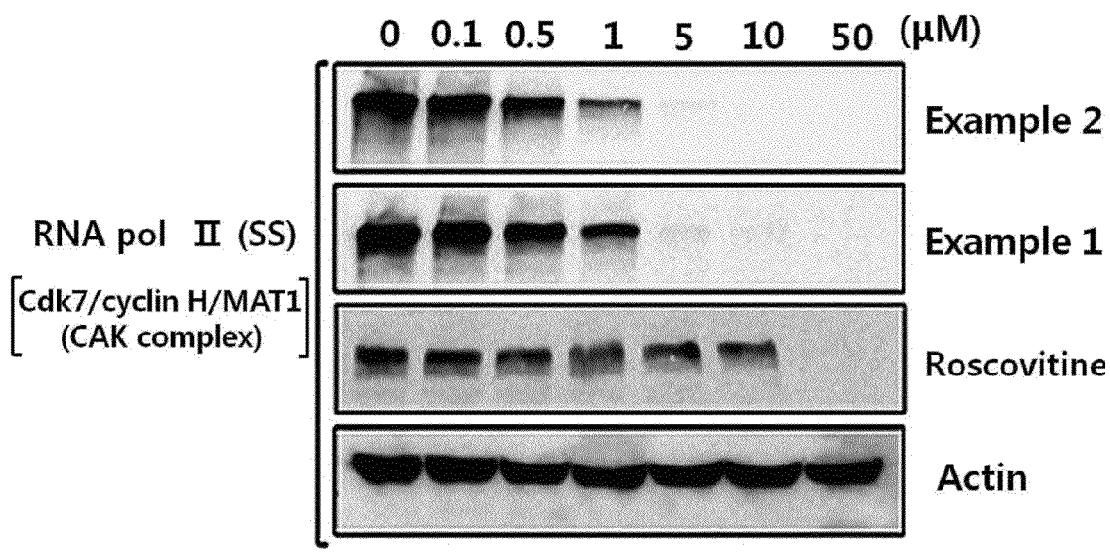
FIG. 9 is a diagram illustrating the result of Western blotting analyzing the Cdk7 activity induced by the compound of an example of the present invention.
Figure 10:
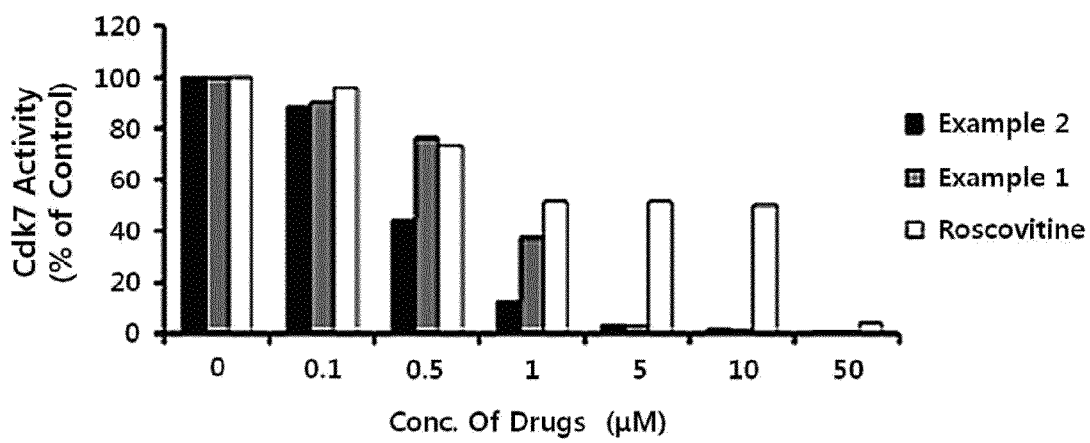
FIG. 10 is a graph illustrating the quantification of the result of Western blotting analyzing the Cdk7 activity induced by the compound of an example of the present invention.
Figure 11:
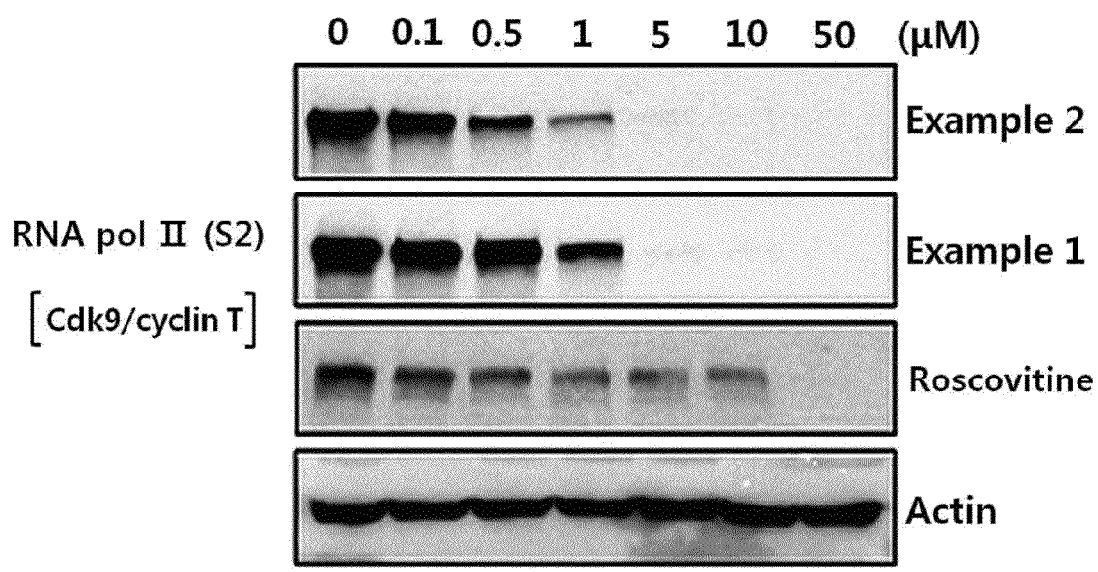
FIG. 11 is a diagram illustrating the result of Western blotting analyzing the Cdk9 activity induced by the compound of an example of the present invention.
Figure 12:
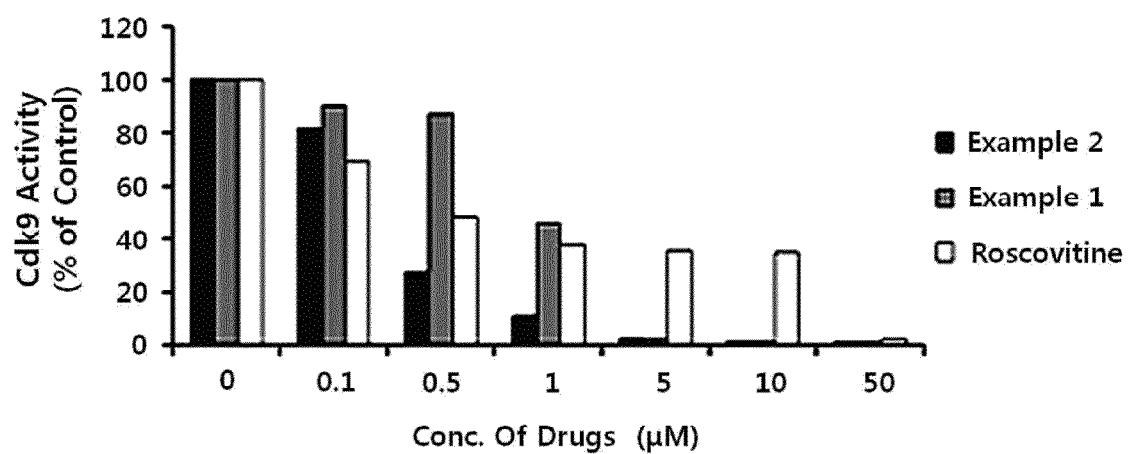
FIG. 12 is a graph illustrating the quantification of the result of Western blotting analyzing the Cdk9 activity induced by the compound of an example of the present invention.

After treating the compound of Example 2 to SNU-354 cells, cell pellet was lysed with lysis buffer (0.5% triton X-100, 20 mM Tris-HCl (pH 7.5), 2 mM magnesium chloride, 1 mM DTT, 1 mM EGTA, 50 mM β-glycerophosphate, 25 mM sodium fluoride, 1 mM $Na_3VO_4$, 2 μg/mL leupeptin, 2 μg/mL pepstatin A, 100 μg/mL phenylmethylsulfonyl fluoride, and 1 μg/mL antipain) at 4° C. for 1 hour, followed by quantification of protein. A proper amount of protein was electrophoresed on SDS-PAGE gel and then transferred onto polyvinylidene difluoride membrane (Millipore Co., Bedford, Mass.). The membrane was reacted in inhibiting solution (PBS, 5% skim milk, 0.1% tween-20) at room temperature for 1~2 hours. The membrane was reacted with the primary antibody (goat anti-phospho-Rb, rabbit anti-nucleolin) diluted in the inhibiting solution (1:1000). Then, the membrane was washed with PBST, followed by reaction with the proper secondary antibody (horseradish peroxidase (HRP) conjugated) at room temperature for 1 hour. Photosensitization was performed with ECL solution (GE Healthcare, Buckinghamshire, UK) and the results are shown in FIG. 3, FIG. 4, and Table 2.

TABLE 2

| | Treatment time of the compound of Example 2 | Phosphorylation (%) |
| --- | --- | --- |
| p-Nucleolin (Cdk1) | 0 | 100 |
| | 6 | 96.9 |
| | 12 | 11.7 |
| | 18 | 3.1 |
| | 24 | 3.0 |
| p-Rb(Cdk2) | 0 | 100 |
| | 6 | 3.6 |
| | 12 | 2.7 |
| | 18 | 0.6 |
| | 24 | 0.3 |

As shown in Table 2, the phosphorylation of Cdk1 over p-nucleolin was rapidly reduced after 12 hours from the treatment began. The phosphorylation of Cdk2 over p-RB was also rapidly reduced after 6 hours from the treatment began and reached almost 0%. The above results suggest that the compound of Example 2 of the present invention inhibits Cdk1 and Cdk2 activities.

The compound of the present invention was confirmed to inhibit Cdk1 and Cdk2 activities significantly via in vitro kinase assay and Western blotting. Therefore, the compound of the present invention can be effectively used for preventing or treating hepatocellular carcinoma.

<1-3> In Vitro Kinase Assay of Cdk7 and Cdk9

The following experiments were performed to investigate whether or not the compound of the present invention could inhibit Cdk7 and Cdk9 activities.

<1-3-1> In Vitro Kinase Assay

To kinase assay buffer were added RNA Pol II-CTD-GST protein (Jena Bioscience, Germany) as a substrate, Cdk9/cyclin T1 or Cdk7/cyclin H/MAT1 recombinant protein (Upstate) as an enzyme, 2.5 μCi [γ-32P]ATP, and 100 μM MgAc/ATP. The total reaction volume was adjusted to 50 μl. Kinase assay reaction was induced at 30° C. for 20 minutes. Upon completion of the reaction, electrophoresis was performed on 8% SDS-polyacrylamide gel. The activities of Cdk7 and Cdk9 over the concentrations of the compounds of Example 1 and Example 2 were confirmed by autoradiography and the results are shown in FIG. 5~FIG. 8 and Table 3.

The intensity of bands was analyzed by densitometry (GS-800, Bio-Rad).

TABLE 3

| | Compound | Conc. (nM) | Cdk7 activity | Cdk9 activity |
| --- | --- | --- | --- | --- |
| Comparative group | Roscosvitine | 0 | 100 | 100 |
| | | 10 | 92.0 | 55.6 |
| | | 100 | 43.4 | 44.6 |
| | | 1000 | 17.4 | 42.2 |
| Treatment group | Compound of Example 1 | 0 | 100 | 100 |
| | | 10 | 41.8 | 15.8 |
| | | 100 | 10.8 | 1.0 |
| | | 1000 | 5.8 | 0.1 |
| | Compound of Example 2 | 0 | 100 | 100 |
| | | 10 | 92.2 | 95.4 |
| | | 100 | 91.1 | 40.5 |
| | | 1000 | 6.5 | 3.3 |

Table 3 presents the results of the experiment in which roscosvitine known as a Cdk7 and Cdk9 inhibitor was set as the comparative control and the compound of Example 1 and the compound of Example 2 were treated to Cdk7 and Cdk9.

As shown in Table 3, when roscosvitine known as a Cdk inhibitor was treated at the concentration of 10~1000 nM, Cdk7 activity was reduced to 92%~17.4% and Cdk9 activity was reduced to 55.6%~42.2%. In the meantime, when the compound of Example 1 was treated at the concentration of 10~1000 nM, Cdk 7 activity was reduced to 41.8%~5.8% and Cdk9 activity was reduced to 15.8%~0.1%, indicating that the compound of the present invention demonstrated better activity than roscosvitine, the conventional Cdk inhibitor. When the compound of Example 2 of the present invention was treated at the concentration of 10~1000 nM, Cdk7 activity was reduced to 92.2%~6.5% and Cdk9 activity was reduced to 95.4%~3.3%, which was also higher activity than when roscosvitine was treated. From the above results, it was confirmed that the compound of the present invention inhibited cdk7 and Cdk9 activities significantly.

<1-3-2> Western Blotting

Experiment was performed by the same manner as described in step 2 of Experimental Example 1 except that rabbit anti-phospho RNA Pol II (Ser 5) and rabbit anti-phospho RNA Pol II (Ser 2) (from Bethyl, TX, USA) were used as primary antibodies. The results are shown FIG. 9~FIG. 12, and Table 4 and Table 5.

TABLE 4

|  | Compound | Conc. (nM) | Cdk7 activity |
|---|---|---|---|
| Comparative group | Roscosvitine | 0 | 100 |
|  |  | 0.1 | 96.0 |
|  |  | 0.5 | 73.1 |
|  |  | 1 | 51.5 |
|  |  | 5 | 51.6 |
|  |  | 10 | 49.9 |
|  |  | 50 | 4.0 |
| Treatment group | Compound of Example 1 | 0 | 100 |
|  |  | 0.1 | 90.1 |
|  |  | 0.5 | 76.3 |
|  |  | 1 | 37.6 |
|  |  | 5 | 3.0 |
|  |  | 10 | 1.7 |
|  |  | 50 | 0.3 |
|  | Compound of Example 2 | 0 | 100 |
|  |  | 0.1 | 88.4 |
|  |  | 0.5 | 44.0 |
|  |  | 1 | 12.7 |
|  |  | 5 | 3.3 |
|  |  | 10 | 1.6 |
|  |  | 50 | 0.6 |

As shown in Table 4, as the concentration of the control roscosvitine was raised from 0 nM to 10 nM, the Cdk7 activity was inhibited dose-dependently up to 50%. As the concentration of the compound of Example 1 was raised from 0 nM to 50 nM, the Cdk7 activity was also inhibited dose-dependently. Particularly, when the concentration of the compound was 10 nM or higher, the Cdk7 activity reached almost 0%. As the concentration of the compound of Example 2 was raised from 0 nM to 50 nM, the Cdk 7 activity was also reduced dose-dependently and particularly from the concentration of 5 nM, the activity was almost 0%, indicating that the compound of Example 2 had excellent Cdk7 inhibiting effect. From the above results, it was confirmed that the compounds of Example 1 and Example 2 of the present invention had excellent Cdk7 inhibiting effect.

TABLE 5

|  | Compound | Conc. (nM) | Cdk9 activity |
|---|---|---|---|
| Comparative group | Roscosvitine | 0 | 100 |
|  |  | 0.1 | 69.3 |
|  |  | 0.5 | 48.5 |
|  |  | 1 | 38.1 |

TABLE 5-continued

|  | Compound | Conc. (nM) | Cdk9 activity |
|---|---|---|---|
|  |  | 5 | 35.7 |
|  |  | 10 | 34.6 |
|  |  | 50 | 2.2 |
| Treatment group | Compound of Example 1 | 0 | 100 |
|  |  | 0.1 | 90.4 |
|  |  | 0.5 | 87.0 |
|  |  | 1 | 46.1 |
|  |  | 5 | 1.9 |
|  |  | 10 | 1.3 |
|  |  | 50 | 0.2 |
|  | Compound of Example 2 | 0 | 100 |
|  |  | 0.1 | 81.5 |
|  |  | 0.5 | 27.3 |
|  |  | 1 | 11.0 |
|  |  | 5 | 2.2 |
|  |  | 10 | 1.1 |
|  |  | 50 | 0.7 |

As shown in Table 5, as the concentration of the control roscosvitine was raised from 0 nM to 10 nM, the Cdk activity was reduced from 100% to 34.6% and particularly when the control was treated at high concentration of 50 nM, the Cdk 9 activity was significantly reduced to 2.2%. In the meantime, the compound of Example 2 of the present invention inhibited the Cdk9 activity to 11% with the concentration of 1 nM and the Cdk9 activity was hardly observed at the concentration of 5 μM, indicating that the compound of Example 2 had excellent Cdk9 inhibiting effect. The compound of Example 1 also inhibited the Cdk9 activity dose-dependently and particularly the compound could almost perfectly inhibit the Cdk9 activity at the concentration of 5 μM or up. From the above results, it was confirmed that the compounds of the present invention have excellent Cdk9 inhibiting effect.

The compound of the present invention was confirmed via in vitro kinase assay and Western blotting to inhibit Cdk7 and Cdk9 activities significantly. Therefore, the compound of the present invention can be effectively used for preventing or treating hepatocellular carcinoma.

<1-4> Measurement of Mcl-1, Survivin, XIAP mRNA and Protein

Western blotting and RT-PCR were performed as follows in order to investigate the effect of the compound of the present invention on the amount of mRNA and proteins of those factors necessary for cell survival such as Mcl-1, survivin, and XIAP.

<1-4-1> Western Blotting

Experiment was performed by the same manner as described in step 2 of Experimental Example 1 except that rabbit anti-Mcl-1 (from Santa Cruz Biochemicals, CA, USA), rabbit anti-survivin, rabbit anti-XIAP (from Cell Signaling, MA, USA), and rabbit anti-Actin (from Sigma, USA) were used as primary antibodies. The results are shown in FIG. 13.

Figure 13:
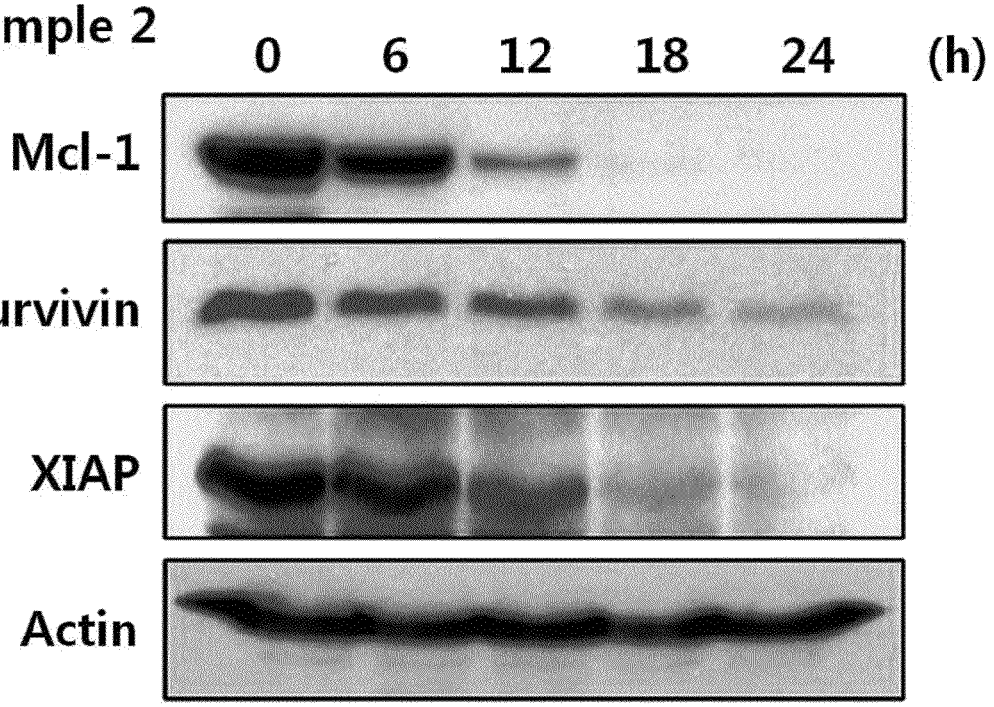
FIG. 13 is a diagram illustrating the result of Western blotting analyzing the down-regulations of Mcl-1, survivin, and XIAP caused by the compound of an example of the present invention.

As shown in FIG. 13, it was confirmed that the compound of Example 2 down-regulated those molecules necessary for cell survival of SNU-354 such as Mcl-1, Survivin, and XIAP. This meant the compound induced apoptosis of SNU-354, the hepatocellular carcinoma cell line. Therefore, it was confirmed that the compound of Example 2 had hepatocellular carcinoma suppressing effect.

<1-4-2> RT-PCR

Figure 14:
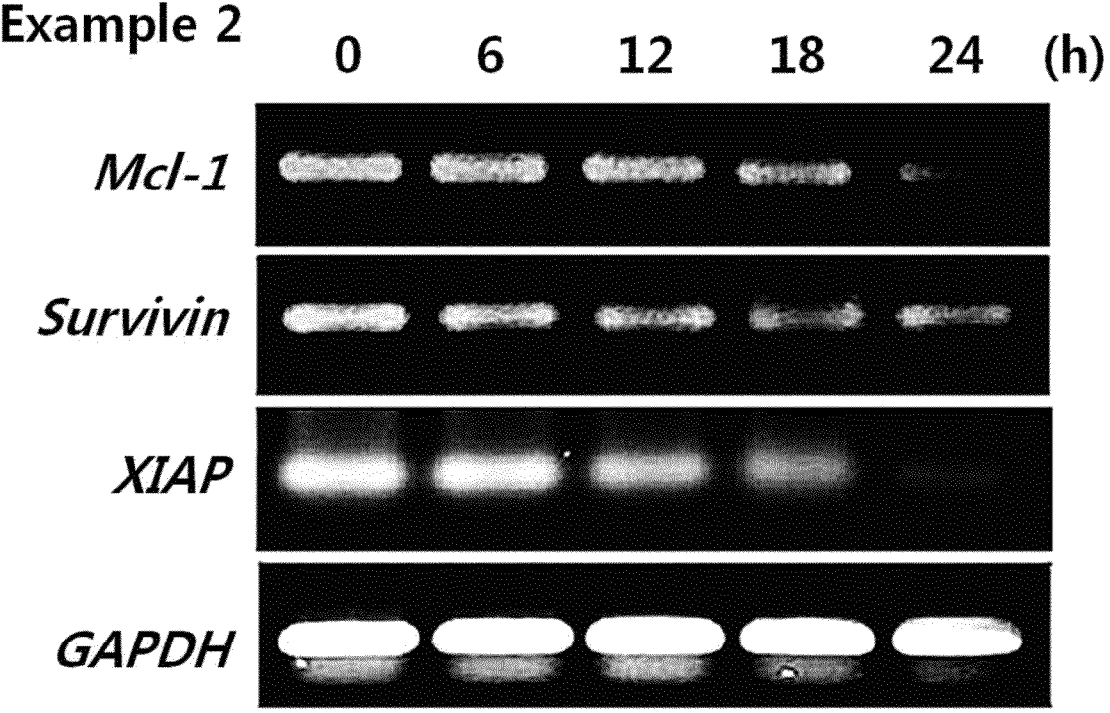
FIG. 14 is a diagram illustrating the result of PCR analyzing the down-regulations of Mcl-1, survivin, and XIAP caused by the compound of an example of the present invention.

Total RNA was extracted from SNU-354 cells treated with the compound of Example 2 according to the conventional method. For reverse transcription, 5 μg of the extracted RNA and M-MLV reverse transcriptase (Promega Corporation, WI, USA) were used. Reverse Transcription was induced at 37° C. for 1 hour, followed by further reaction at 95° C. for 5 minutes. For PCR, 5 µl of cDNA obtained from the reverse transcription was used as a template and Taq DNA polymerase was used. Total reaction volume was 50 µl. PCR was performed as follows; predenaturation at 95° C. for 5 minutes, denaturation at 95° C. for 1 minute, annealing at 56° C. for 1 minute, polymerization at 72° C. for 1 minute, 30 cycles from denaturation to polymerization, and final extension at 72° C. for 10 minutes. After PCR, the PCR products were analyzed by electrophoresis on 1% agarose gel. The results are shown in FIG. 14. The forward primer for Mcl-1 was 5'-CGG TAA TCG GAC TCA ACC TC-3' (SEQ ID NO: 1) and the reverse primer was 5'-CCT CCT TCT CCG TAG CCA A-3' (SEQ ID NO: 2). The forward primer for XIAP was 5'-AGT GGT AGT CCT GTT TCA GCA TCA-3' (SEQ ID NO: 3) and the reverse primer was 5'-CCG CAC GGT ATC TCC TTC A-3' (SEQ ID NO: 4). The forward primer for survivin was 5'-TGC CTG GCA GCC CTT TC-3' (SEQ ID NO: 5) and the reverse primer was 5'-CCT CCA AGA AGG GCC AGT TC-3' (SEQ ID NO: 6). The forward primer for GAPDH was 5'-GAA GGT GAA GGT CGG AGT-3' (SEQ ID NO: 7) and the reverse primer was 5'-GAA GAT GGT GAT GGG ATT TC-3' (SEQ ID NO: 8). All the primers used herein were provided from BIONICS (Seoul, Republic of Korea).

As shown in FIG. 14, the compound of Example 2 down-regulated those molecules necessary for the survival of SNU-354 cells such as Mcl-1, survivin, and XIAP and such reduction was attributed to the decrease of mRNA (resulted from the inhibition of transcription). This result indicates that the compound of Example 2 induces apoptosis of SNU-354 cells, the hepatocellular carcinoma cells, which is another words the compound of the present invention has hepatocellular carcinoma inhibiting activity.

The compound of the present invention down-regulated Mcl-1, survivin, and XIAP proteins in SNU-354 cells and such reduction of intracellular proteins was attributed to the decrease of mRNA, which was confirmed by RT-PCR. That is, the compound of the present invention inhibited Cdk7 and Cdk 9 activities in SNU-354 cells and hence inhibited RNA polymerase 2 activity. Therefore, the compound of the present invention can inhibit the transcriptions of those molecules necessary for the cell survival such as Mcl-1, survivin, and XIAP, so that it can be effectively used for the prevention and treatment of hepatocellular carcinoma.

<1-5> Measurement of HCC Cell Growth

Following experiments were performed to investigate the effect of the compound of the present invention on HCC cell growth.

<1-5-1> MTT Assay

Figure 15:
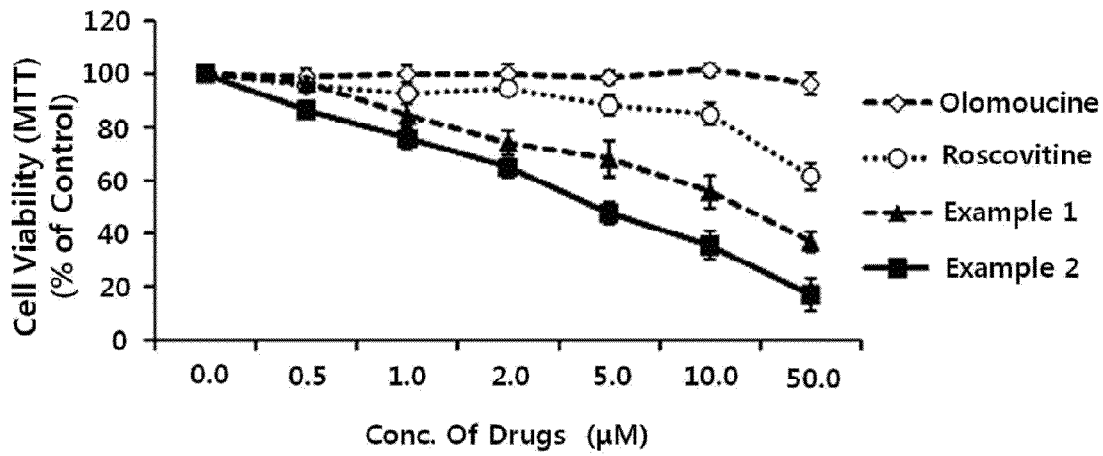
FIG. 15 is a diagram illustrating the result of MTT assay analyzing the cell viability affected by the compound of an example of the present invention.

Cell viability was measured by MTT assay. SNU-354 cells in the log phase of cell growth curve were distributed in a 24-well plate at the density of $2 \times 10^4$ cells/well. 24 hours later, sample compounds (compound of Example 1, compound of Example 2, roscovitine or olomoucine) were treated thereto at different concentrations. After allowing enough time for reaction, MTT reagent (MTT dissolved in PBS at the concentration of 5 mg/mL) (Sigma-Aldrich, USA) was added to each well, followed by reaction at 37° C. for 3 hours. Then, the supernatant was eliminated and the precipitated formazan crystals were dissolved in dimethyl sulfoxide, followed by measurement of absorbance with ELISA plate reader. The results are shown in FIG. 15 and Table 6.

TABLE 6

| | | Cell viability (%) | | | |
|---|---|---|---|---|---|
| | | Olomoucine | Roscosvitine | Compound of Example 1 | Compound of Example 2 |
| Conc. (µM) | 0 | 100 | 100 | 100 | 100 |
| | 0.5 | 98.9 | 95.9 | 96.4 | 86.3 |
| | 1.0 | 99.9 | 92.5 | 84.3 | 75.5 |
| | 2.0 | 99.9 | 94.5 | 74.0 | 64.7 |
| | 5.0 | 98.5 | 87.9 | 68.0 | 47.6 |
| | 10.0 | 101.4 | 84.7 | 55.6 | 35.4 |
| | 50.0 | 96.0 | 61.4 | 36.6 | 16.8 |

In Table 6, SNU-354 cell viability over the concentrations of the conventional Cdk inhibitors olomoucine and roscosvitine and the compounds of Example 1 and Example 2 is presented. Overall, cell growth was inhibited by those compounds dose-dependently. Cell viability in the group treated with olomoucine at the highest concentration was 96%, and cell viability in the group treated with roscosvitine was 61.4%. In the meantime, cell viabilities in the groups treated with the compounds of Example 1 and Example 2 of the present invention were respectively 36.6% and 16.8%. The above results indicate that the inhibition effect of the compounds of the present invention on cell growth is greater than that of the conventional Cdk inhibitors olomoucine and roscosvitine. That is, cell growth of SNU-354 was more effectively inhibited by the compound of the present invention and the inhibition effect was most apparent by the compound of Example 2 that demonstrated the lowest cell viability of 16.8%.

<1-5-2> $^3$H-Thymidine Incorporation Assay

Figure 16:
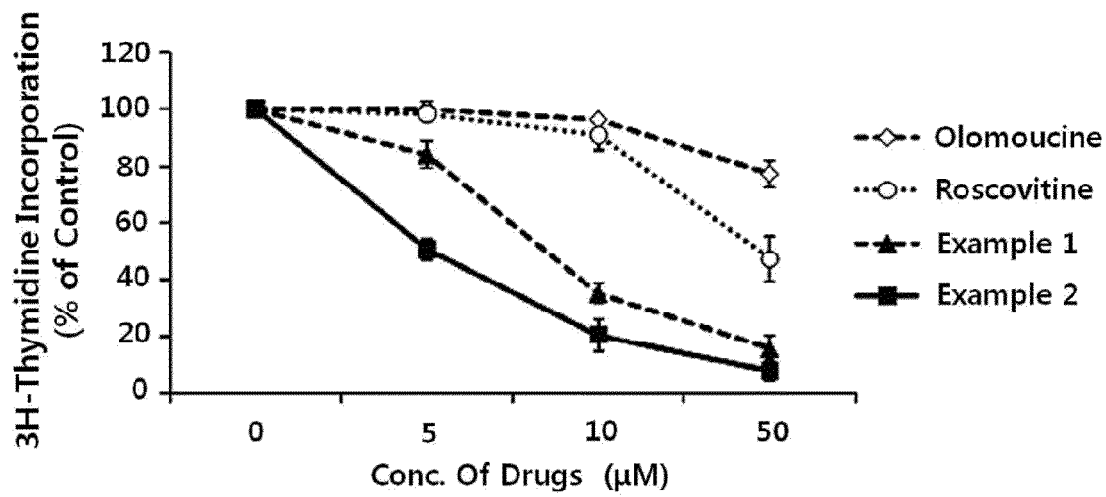
FIG. 16 is a diagram illustrating the result of $^3$H-thymidine incorporation assay analyzing the cell viability affected by the compound of an example of the present invention.

SNU-354 cells were distributed in a 6-well plate at the density of $5 \times 10^4$ cells/well, followed by culture in FBS-free medium for 24 hours. 24 hours later, the medium was replaced with the fresh one supplemented with FBS, the compounds of Examples 1 and 2 at different concentrations and 1 µCi/mL [$^3$H]dT (GE Healthcare, UK). 18~24 hours later, the cells were washed with cold PBS and then fixed with cold 5% trichloroacetic acid. DNA was lysed in 10.25 N sodium hydroxide at 37° C. for 1 hour. Then, [$^3$H]dT incorporated during intracellular DNA synthesis was measured by LSC (liquid scintillation counting). Intracellular DNA synthesis measured above was used as index for the evaluation of cell viability. The results are shown in FIG. 16 and Table 7.

TABLE 7

| | | $^3$H-thymidine incorporation (%) | | | |
|---|---|---|---|---|---|
| Compound | | Olomoucine | Roscosvitine | Compound of Example 1 | Compound of Example 2 |
| Conc. (µM) | 0 | 100 | 100 | 100 | 100 |
| | 5.0 | 99.7 | 98.2 | 84.0 | 50.7 |
| | 10.0 | 96.3 | 91.0 | 35.2 | 20.4 |
| | 50.0 | 77.2 | 47.2 | 15.8 | 8.0 |

In Table 7, the results of $^3$H-thymidine incorporation over the concentrations of the conventional Cdk inhibitors olomoucine and roscosvitine and the compounds of Examples 1 and 2 of the present invention are presented. Higher $^3$H-thymidine incorporation indicates higher cell viability. Overall, as the concentrations of those compounds increased, cell viability decreased. In particular, $^3$H-thymidine incorporation in the group treated with olomoucine at the highest concentration was 77.2%. In the group treated with roscosvitine, ³H-thymidine incorporation was 47.2%. In the meantime, ³H-thymidine incorporation was 15.8% and 8% respectively in the group treated with the compound of Example 1 or Example 2. That is, ³H-thymidine incorporation indicating cell viability was lower in the group treated with the compound of Example 1 or Example 2 of the present invention than in the group treated with the conventional Cdk inhibitors olomoucine and roscosvitine. Therefore, it was confirmed that the compounds of the present invention can inhibit the cell growth of SNU-354 effectively.

Since the compounds of the present invention can inhibit the cell growth of SNU-354 more effectively than other conventional Cdk inhibitors, they can be effectively used for preventing or treating hepatocellular carcinoma.

<1-6> Effect on Inducing HCC Cell Apoptosis

Following experiments were performed to investigate whether or not the compound of the present invention could induce HCC cell apoptosis.

<1-6-1> Western Blotting

Figure 17:
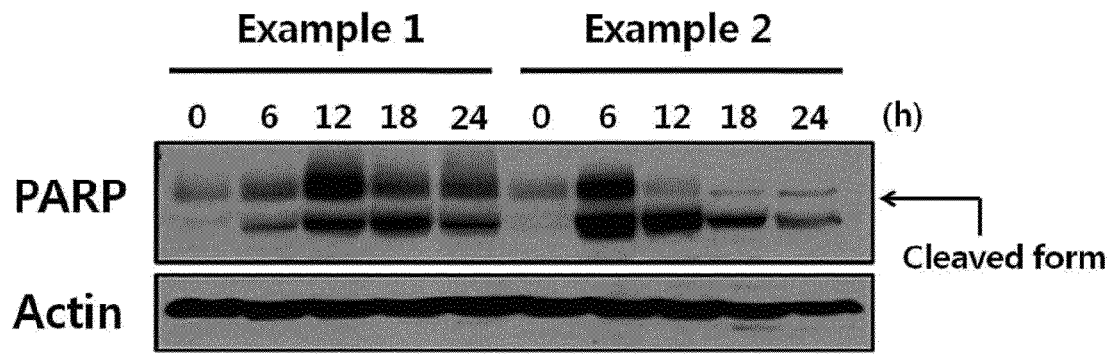
FIG. 17 is a diagram illustrating the result of Western blotting analyzing the PARP cleavage effect of the compound of an example of the present invention.

Experiment was performed by the same manner as described in step 2 of Experimental Example 2 except that rabbit anti-PARP was used as the primary antibody and the results are shown in FIG. 17.

As shown in FIG. 17, the compounds of Examples 1 and 2 could induce apoptosis of SNU-354 cells confirmed by PARP cleavage experiment. In particular, the compound of Example 2 caused PARP cleavage after 6 hours from the treatment. The compound of Example 1 caused PARP cleavage after 12 hours from the treatment. The above results indicate that the compound of Example 2 induce apoptosis more significantly than the compound of Example 1.

<1-6-2> Measurement of Caspase-3 Activity

Figure 18:
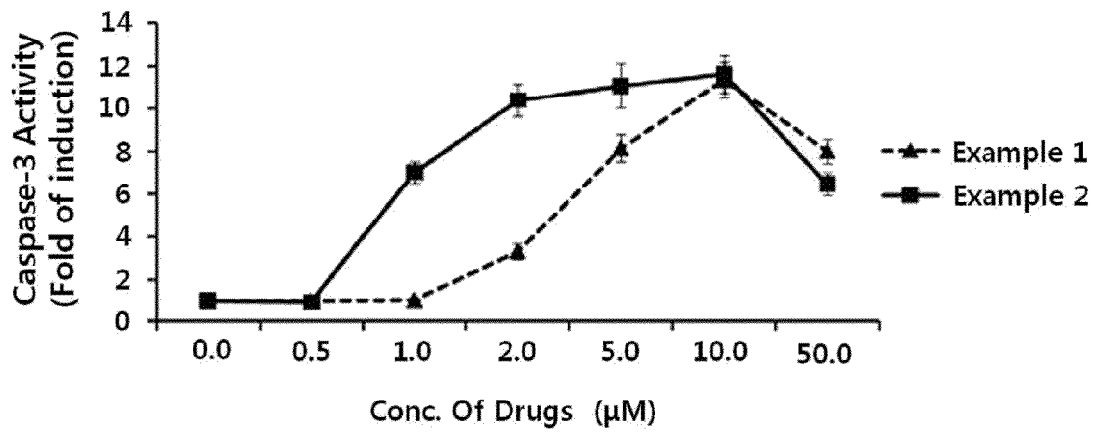
FIG. 18 is a diagram illustrating the measurement of caspase-3 activity according to the concentrations of the compound of an example of the present invention.

SNU-354 cells treated with the compounds of Examples 1 and 2 were lysed with lysis buffer (0.5% triton X-100, 20 mM Tris-HCl (pH 7.5), 2 mM magnesium chloride, 1 mM DTT, 1 mM EGTA, 50 mM β-glycerophosphate, 25 mM sodium fluoride, 1 mM $Na_3VO_4$, 2 μg/mL leupeptin, 2 μg/mL pepstatin A, 100 μg/mL phenylmethylsulfonyl fluoride, 1 μg/mL antipain). The protease analysis buffer necessary for the reaction (20 mM HEPES (pH 7.5), 10% glycerol, 2 mM DTT) was mixed with 20 μM Ac-DEVD-AMC (BD Biosciences, CA, USA) and cell lysates, followed by reaction at 37° C. for 1 hour. Upon completion of the reaction, caspase-3 activity was measured at 380 nm of excitation and 460 nm of emission with spectrofluorometer (TECAN, Switzerland) and the results are shown in FIG. 18 and Table 8.

TABLE 8

|  |  | ³H-thymidine incorporation (%) | |
|---|---|---|---|
|  |  | Compound of Example 1 | Compound of Example 2 |
| Conc. (μM) | 0 | 1.0 | 1.0 |
|  | 0.1 | 1.0 | 0.9 |
|  | 0.5 | 1.0 | 7.0 |
|  | 1.0 | 3.3 | 10.4 |
|  | 5.0 | 8.2 | 11.1 |
|  | 10.0 | 11.4 | 11.6 |
|  | 50.0 | 8.0 | 6.5 |

In Table 8, caspase-3 activity over the concentrations of the compounds of Examples 1 and 2 was presented. The highest caspase-3 activity was observed at the concentration of 10.0 μM of both compounds. In the group treated with the compound of Example 1 at the concentration of 1.0 uM and up, caspase-3 activity became three times as high as that of the control. In the group treated with the compound of Example 2 at the concentration of 0.5 uM and up, caspase-3 activity became 7 times as high as that of the control. The above results indicate that caspase-3 activity is increased by the compounds of the present invention dose-dependently.

<1-6-3> FACS Analysis

Figure 19:
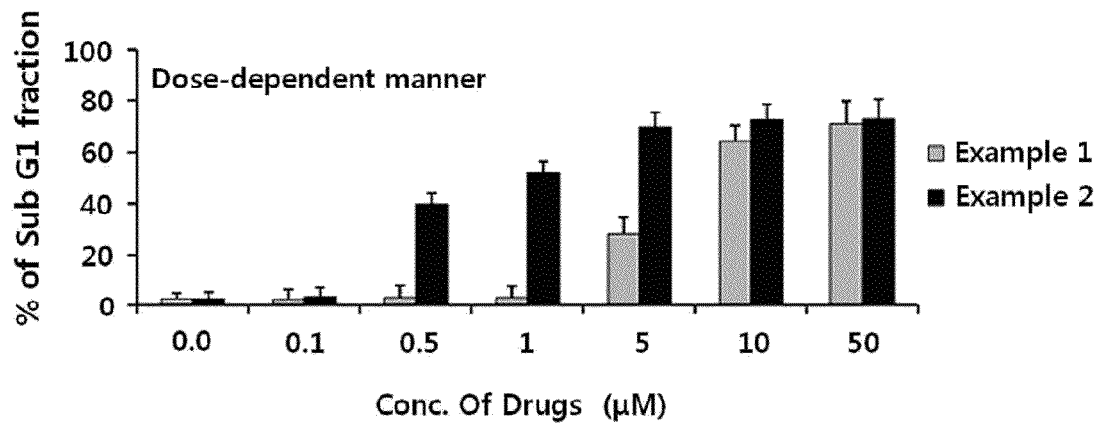
FIG. 19 is a diagram illustrating the result of FACS assay analyzing the changes of sub G1 ratio of SNU-354 cells according to the concentrations of the compound of an example of the present invention.
Figure 20:
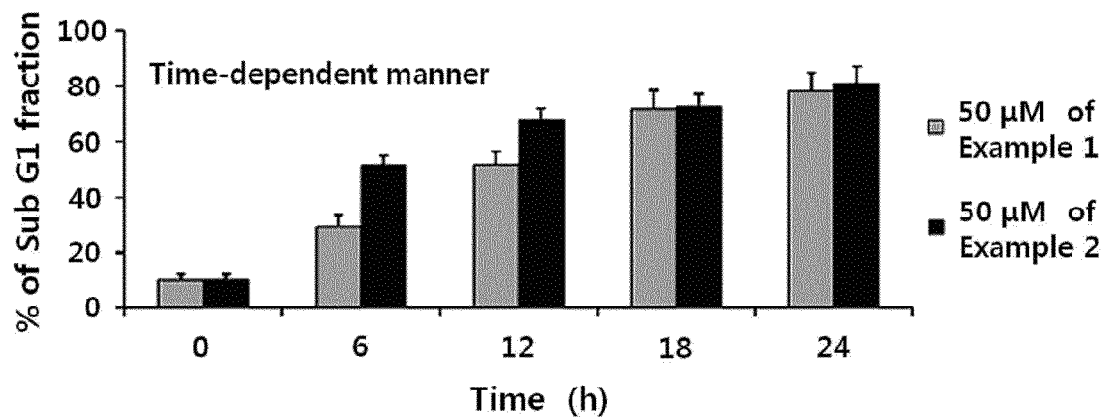
FIG. 20 is a diagram illustrating the result of FACS assay analyzing the changes of sub G1 ratio of SNU-354 cells over the time affected by the compound of an example of the present invention.

SNU-354 cells were seeded in 90 mm dish, to which the compounds of Examples 1 and 2 were treated at proper concentrations for 24 hours. The cells were collected and washed with cold PBS, followed by reaction in 500 μl of cold 70% ethanol at 4° C. for overnight to fix the cells. The cells were washed with 500 μl of PBS three times, followed by reaction with 500 μl of PBS containing 50 μg/mL propidium iodide (P1) and 50 μl of 1 mg/mL RNAse A at room temperature for 30 minutes in the darkness. Fluorescence of the P1 stained cell was measured by using caliber flow cytometer and cell quest program (Becton Dickinson Immunocytometry Systems, CA, USA). Sub G1 ratio changes of HCC SNU-354 cells induced by the compounds of Examples 1 and 2 were measured by FACS analysis. The results are shown in FIG. 19, FIG. 20, Table 9 and Table 10.

TABLE 9

|  |  | sub G1 ratio (%) | |
|---|---|---|---|
|  |  | Compound of Example 1 | Compound of Example 2 |
| Conc. (μM) | 0 | 3.0 | 3.0 |
|  | 0.1 | 2.7 | 3.8 |
|  | 0.5 | 3.2 | 39.6 |
|  | 1 | 3.5 | 52.0 |
|  | 5 | 28.1 | 69.8 |
|  | 10 | 64.2 | 72.6 |
|  | 50 | 71.1 | 73.1 |

As shown in Table 9, sub G1 ratio was rapidly increased by the compound of Example 1 at the concentration of 5 μM, while sub G1 ratio was rapidly increased by the compound of Example 2 at the concentration of 0.5 μM. That is, the compounds induce apoptosis of SNU-354 cells rapidly from the said concentrations.

TABLE 10

|  |  | sub G1 ratio (%) | |
|---|---|---|---|
|  |  | Compound of Example 1 | Compound of Example 2 |
| Time (h) | 0 | 10.3 | 10.3 |
|  | 6 | 29.1 | 51.6 |
|  | 12 | 51.8 | 67.6 |
|  | 18 | 71.7 | 72.3 |
|  | 24 | 78.1 | 81.2 |

Table 10 presents sub G1 ratio changes over the time in the group treated with the compound of Example 1 or Example 2 at the concentration of 50 μM. Sub G1 ratio was increased over the time in the group treated with the compounds of the present invention, indicating that apoptosis was induced by the compounds time-dependently.

Since the compound of the present invention induces apoptosis of HCC SNU-354 cells, it can be effectively used for preventing or treating hepatocellular carcinoma.

Experimental Example 2

Animal Test

<2-1> SNU-354 Cancer Xenograft

Figure 21:
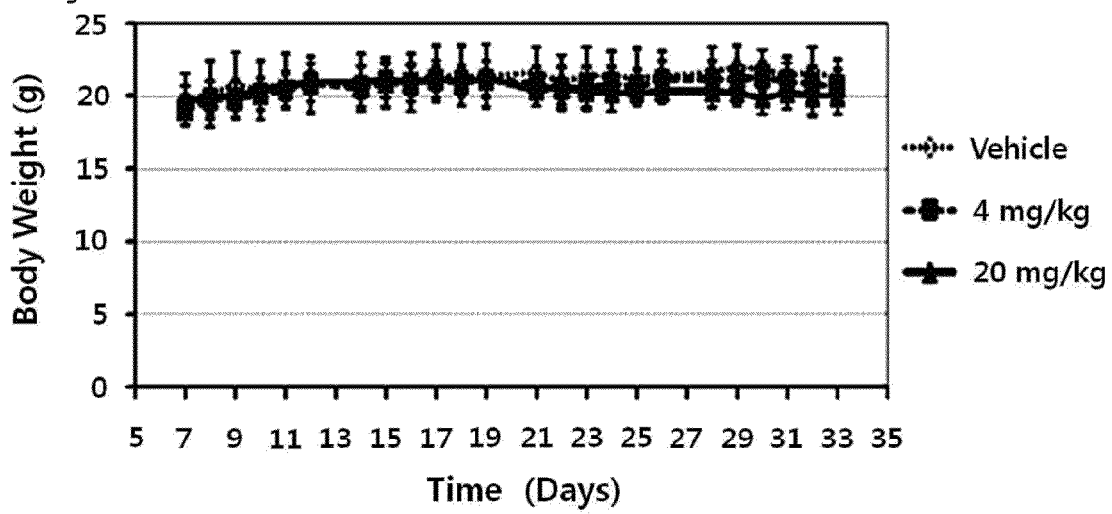
FIG. 21 is a diagram illustrating the weight changes of test animals over the concentrations of the compound of an example of the present invention.
Figure 22:
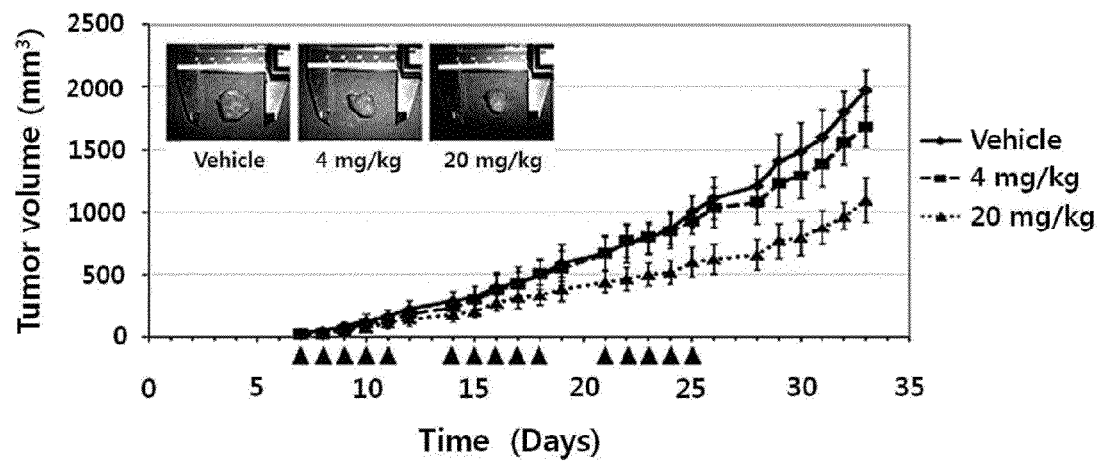
FIG. 22 is a diagram illustrating the growth of xenografted tumor in the group treated with the compound of an example of the present invention.

Male nude mice at 5~6 weeks were purchased from Central Lab. Animal Inc. (Republic of Korea). The mice were raised in the test animal laboratory at College of Pharmacy, Seoul National University. All the experiments with test animals were performed by the protocol set by Institute of Laboratory Animal Resources, Seoul National University. $1 \times 10^7$ cells of the human hepatocellular carcinoma cell line SNU-354 were suspended in 200 µl of PBS, which was injected into the right front paw of the mouse by subcutaneous injection, followed by observation until the xenograft tumor grew to 100±30 mm$^3$. The mice having tumors reaching the proper size were divided into three groups (n=8). One of the groups was used as the control (treated with vehicle) and the other two groups were treated with the compound of Example 2 at the concentrations of 4 mg/kg and 20 mg/kg respectively, once a day for 3 weeks (5 times/week) by intraperitoneal injection. The control group was treated with 5% ethanol and 30% polyethylene glycol 200 (Fluka, Netherlands). The administration schedule was marked on data. Tumor size, body weight and other conditions of the animal were observed every day until the tumor size reached 2000 mm$^3$. The tumor size was calculated by V=a×b×c×π/6 (a=long axis of the tumor, b=short axis of the tumor, c=height of the tumor). 33 days after the treatment, the mice were sacrificed. The xenografted tumor and the liver were extracted and the size and weight of them were measured, which are shown in FIG. 21 and FIG. 22. As a result, it was confirmed that there was no weight change over the concentrations of the compound of Example 2 (FIG. 21). The growth of the xenografted tumor was significantly reduced in the group treated with the compound of Example 2 (4 mg/kg/day, 20 mg/kg/day), compared with that of the vehicle treated control group (FIG. 22). The growth of the tumor in the group treated with the compound of Example 2 at the concentration of 4 mg/kg/day was reduced 15% at average, compared with that of the control, while the growth of the tumor in the group treated with the compound at the concentration of 20 mg/kg/day was reduced 47% at average, compared with that of the control.

TUNEL assay and immunohistochemistry were performed with the extracted tissues.

<2-2> Immunohistochemistry and TUNEL Assay of Caspase-3

Figure 23:
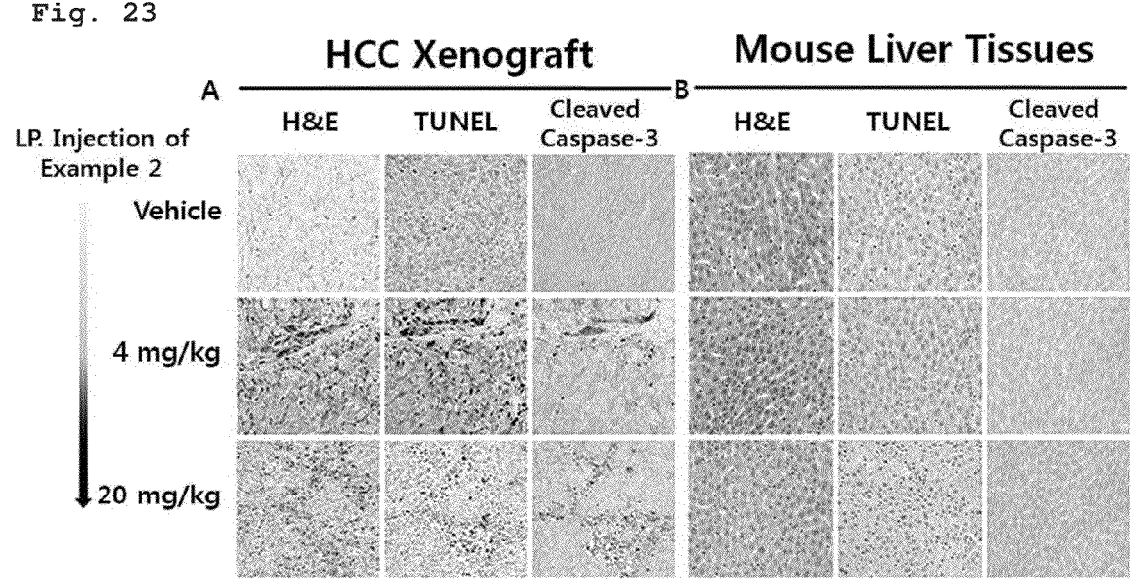
FIG. 23 is a diagram illustrating the results of H&E staining and TUNEL assay with xenografted tumor and liver tissues of the group treated with the compound of an example of the present invention and the expression level of cleaved caspase-3 therein.

All the xenografted tumors and liver tissues extracted above were fixed in 36% formaldehyde solution (Junsei Chemical Co., Ltd, Tokyo, JAPAN), followed by paraffin embedding. The embedded tissues were cut into 5 µm sections. H&E staining and TUNEL assay were performed for examining apoptosis with those sections. The expression of cleaved caspase-3 in the tissue section was measured by using cleaved caspase-3 monoclonal antibody (Cell Signaling, MA, USA). ABC peroxidase (Dako Cytomation California, Inc., CA, USA) labeling was performed for immunological sensitization and the results are shown in FIG. 23. As shown in FIG. 23-A, TUNEL positive spots and caspase-3 positive spots were observed more in the group treated with the compound of Example 2 than in the control. The group treated with high concentration of the compound (20 mg/kg) demonstrated even more spots, indicating that apoptosis induced by the compound of Example 2 leads to the inhibition of the xenografted tumor growth. As shown in FIG. 23-B, it was investigated whether or not the compound of Example 2 could affect normal liver tissues. Particularly, liver tissues were extracted from both the control group and the group treated with the compound of Example 2, followed by TUNEL assay and caspase-3 immunohistochemistry as described in FIG. 23-A. In the normal liver tissues free from xenografted tumor, apoptosis was not observed at all, suggesting that the compound of Example 2 only affect xenografted tumor but not affect normal liver tissues.

Therefore, it was confirmed that the compound of the present invention has liver tissue specific activity, so that it can be effectively used for preventing or treating hepatocellular carcinoma.

Experimental Example 3

Flow Cytometry

Figure 24:
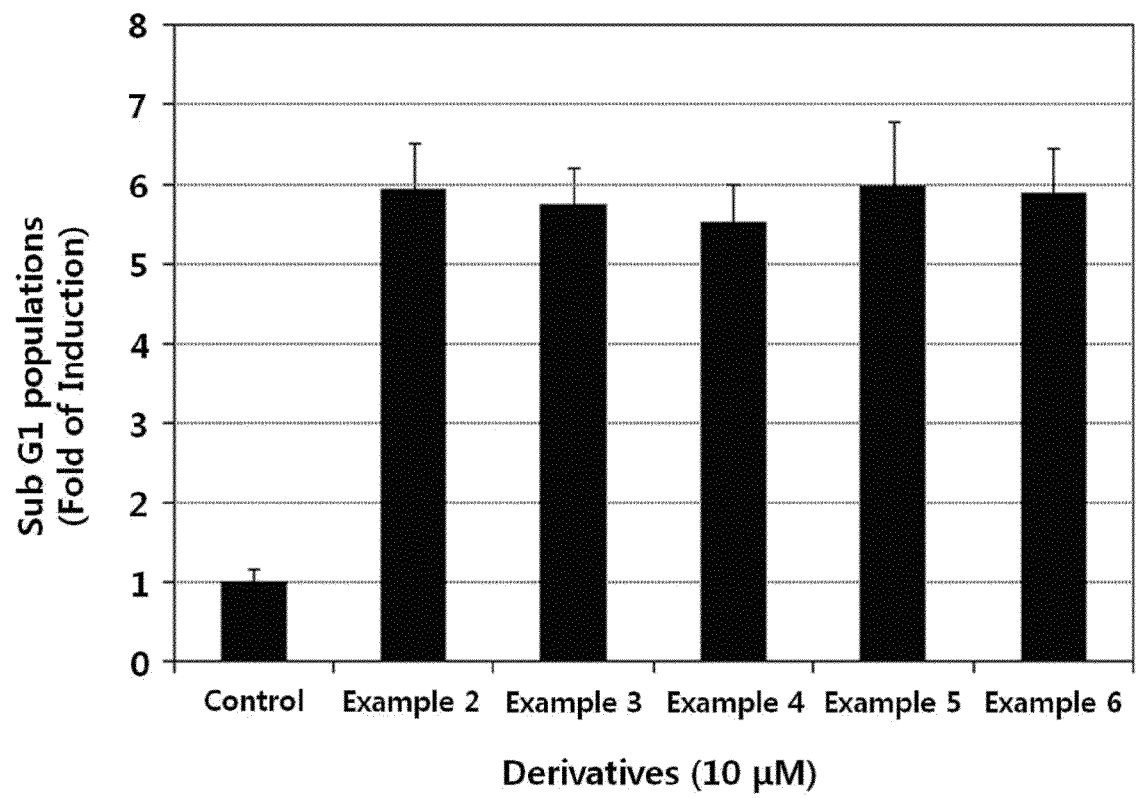
FIG. 24 is a diagram illustrating the result of Sub G1 analysis with SNU-354 cells treated with the compound of an example of the present invention.

SNU-354 cells were seeded in a 90 mm dish, to which vehicle and the compounds of Examples 2~6 were treated at the concentration of 10 µM each for 24 hours. The cells were collected and washed with cold PBS, followed by reaction in 500 µl of cold 70% ethanol at 4° C. for overnight to fix the cells. The cells were washed with 500 µl of PBS three times, followed by reaction with 500 µl of PBS containing 50 µg/mL propidium iodide (P1) and 50 µl of 1 mg/mL RNAse A at room temperature for 30 minutes in the darkness. Fluorescence of the P1 stained cell was measured by using FACS caliber flow cytometer and cell quest program (Becton Dickinson Immunocytometry Systems, CA, USA). Sub G1 ratio changes of SNU-354 cells induced by the compounds were measured by FACS analysis. The results are shown in FIG. 24 and Table 11.

TABLE 11

| Compound | sub G1 ratio change |
|---|---|
| Vehicle | 1.0 |
| Compound of Example 2 | 5.9 |
| Compound of Example 3 | 5.7 |
| Compound of Example 4 | 5.5 |
| Compound of Example 5 | 6.0 |
| Compound of Example 6 | 5.9 |

As shown in Table 11, it was confirmed that the compounds of the present invention had apoptosis inducing effect. Particularly, sub G1 ratio changes over the compounds of Example 2, Example 5, and Example 6 of the present invention were 5.5 times as significant as the control, suggesting that those compounds had excellent apoptosis inducing effect.

Therefore, it was confirmed that the compound of the present invention has excellent apoptosis inducing effect on SNU-354 cells, so that it can be effectively used for preventing or treating hepatocellular carcinoma.

Experimental Example 4

Measurement of Caspase-3 Activity

Figure 25:
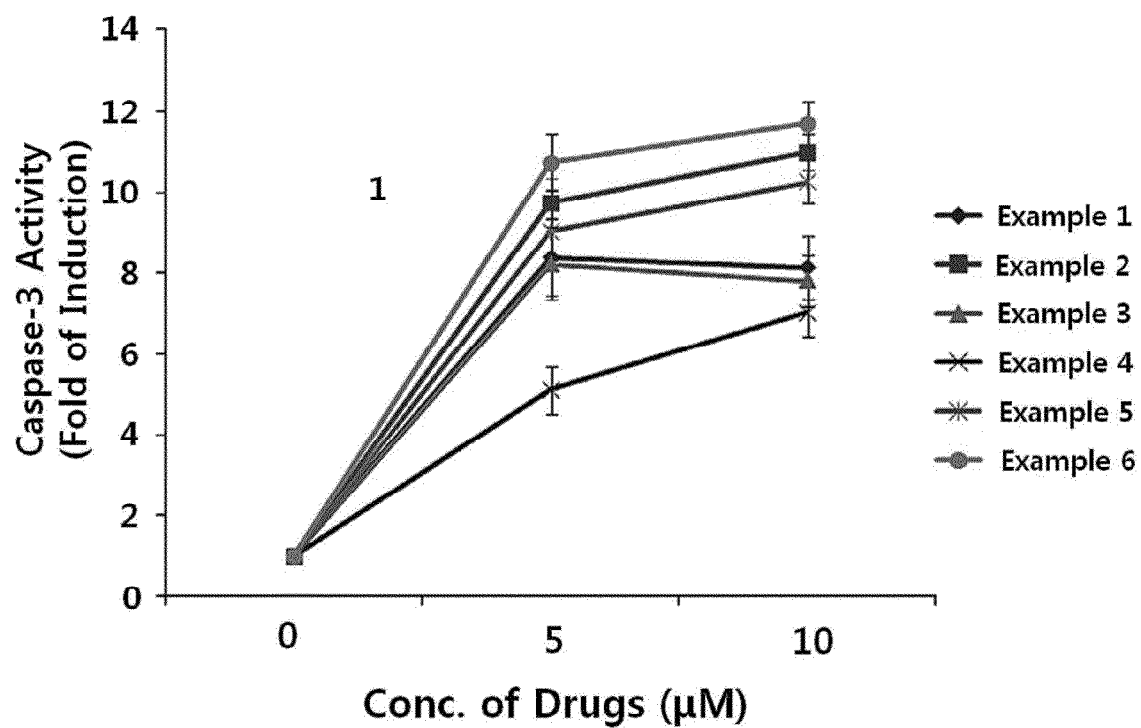
FIG. 25 is a diagram illustrating the caspase-3 activity in SNU-354 cells treated with the compound of an example of the present invention.

SNU-354 cells treated with the compounds of Example 1~Example 6 were lysed with lysis buffer (0.5% triton X-100, 20 mM Tris-HCl (pH 7.5), 2 mM magnesium chloride, 1 mM DTT, 1 mM EGTA, 50 mM β-glycerophosphate, 25 mM sodium fluoride, 1 mM Na$_3$VO$_4$, 2 µg/mL leupeptin, 2 µg/mL pepstatin A, 100 µg/mL phenylmethylsulfonyl fluoride, 1 µg/mL antipain). The protease analysis buffer necessary for the reaction (20 mM HEPES (pH 7.5), 10% glycerol, 2 mM DTT) was mixed with 20 µM Ac-DEVD-AMC (BD Biosciences, CA, USA) and cell lysates, followed by reaction at 37° C. for 1 hour. Upon completion of the reaction, caspase-3 activity was measured at 380 nm of excitation and 460 nm of emission with spectrofluorometer (TECAN, Switzerland) and the results are shown in FIG. 25 and Table 12.

TABLE 12

| Compound | Conc. (μM) | Caspase-3 activity |
|---|---|---|
| Compound of Example 1 | 5 | 8.4 |
| | 10 | 8.1 |
| Compound of Example 2 | 5 | 9.7 |
| | 10 | 11.0 |
| Compound of Example 3 | 5 | 8.2 |
| | 10 | 7.8 |
| Compound of Example 4 | 5 | 5.1 |
| | 10 | 7.0 |
| Compound of Example 5 | 5 | 9.0 |
| | 10 | 10.3 |
| Compound of Example 6 | 5 | 10.7 |
| | 10 | 11.7 |

As shown in Table 12, when the compounds were treated at the concentrations of 5 and 10 μM, caspase-3 activity was increased as the concentrations of the compounds were raised, except when the compounds of Examples 1 and 3 were treated. Particularly, caspase-3 activity was greater when the compounds were treated at the concentrations of 10 μM than when they were treated at the concentrations of 5 μM. Particularly, caspase-3 activity in the group treated with the compounds of Examples 2, 5, and 6 was more than 10.

Therefore, it was confirmed that the compound of the present invention inhibits SNU-354 cell activity, so that it can be effectively used for preventing or treating hepatocellular carcinoma.

The pyrrolopyrimidine carboxamide derivative represented by formula 1 of the present invention can be formulated in different forms according to the purpose of use. In the below were shown examples of methods for preparing different forms comprising the compound represented by formula 1 of the present invention as an active ingredient, but the present invention cannot be limited thereto.

Manufacturing Example 1

Preparation of Pharmaceutical Formulations <1-1> Preparation of Powders

| <1-1> Preparation of powders | |
|---|---|
| pyrrolopyrimidinone carboxamide derivative | 2 g |
| Lactose | 1 g |

Powders were prepared by mixing all the above components, which were filled in airtight packs according to the conventional method for preparing powders.

| <1-2> preparation of tablets | |
|---|---|
| pyrrolopyrimidinone carboxamide derivative | 100 mg |
| Corn starch | 100 mg |
| Lactose | 100 mg |
| Magnesium stearate | 2 mg |

Tablets were prepared by mixing all the above components by the conventional method for preparing tablets.

| <1-3> Preparation of capsules | |
|---|---|
| pyrrolopyrimidinone carboxamide derivative | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

| <1-4> Preparation of injectable solutions | |
|---|---|
| pyrrolopyrimidinone carboxamide derivative | 10 μg/mL |
| Weak HCl BP | until pH 3.5 |
| Injectable NaCl BP | up to 1 mL |

The pyrrolopyrimidine carboxamide derivative of the present invention was dissolved in proper volume of injectable NaCl BP. pH of the prepared solution was regulated as 3.5 by using weak HCl BP. The volume was adjusted by using injectable NaCl BP. The solution was well mixed and filled in 5 mL type I transparent glass ampoules. The ampoules were sealed by melting the glass of opening, followed by autoclave at 120° C. for at least 15 minutes for sterilization.

| <1-5> Preparation of liquid formulations | |
|---|---|
| pyrrolopyrimidinone carboxamide derivative | 100 mg |
| Isomerized sugar | 10 g |
| Mannitol | 5 g |
| Purified water | proper amount |

All the above components were dissolved in purified water. After adding lemon flavor, total volume was adjusted to be 100 mL by adding purified water. Liquid formulations were prepared by putting the mixture into brown bottles and sterilizing thereof by the conventional method for preparing liquid formulations.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A pyrrolopyrimidine carboxamide derivative represented by the following formula 1, or a pharmaceutically acceptable salt thereof:

[Formula 1]

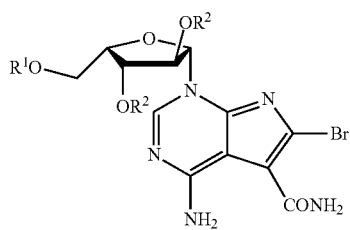

wherein in the Formula 1,
$R^1$ is hydrogen or $R^3C(=O)$;
$R^3$ is $C_1$-$C_6$ straight or branched alkyl, $C_3$-$C_8$ cycloalkyl or phenyl; and
$R^2$ is hydrogen or acetyl.

2. The pyrrolopyrimidine carboxamide derivative or the pharmaceutically acceptable salt thereof according to claim 1, wherein the $R^3$ is methyl, ethyl, propyl, isopropyl, butyl, t-butyl, cyclopentyl, cyclohexyl or phenyl.

3. The pyrrolopyrimidine carboxamide derivative or the pharmaceutically acceptable salt thereof according to claim 1, wherein the compound represented by formula 1 is selected from the group consisting of the following compound (1)-compound (7):

(1) 4-amino-6-bromo-1-((2S,3R,4R,5S)-3,4-dihydroxy-5-(hydroxymethyl)-tetrahydrofuran-2-yl)-1H-pyrrolo[2,3-d]pyrimidine-5-carboxamide;

(2) ((2S,3R,4R,5S)-5-(4-amino-6-bromo-5-carbamoyl-1H-pyrrolo[2,3-d]pyrimidine-1-yl)-3,4-dihydroxy-tetrahydrofuran-2-yl)methyl isobutyrate;

(3) ((2S,3R,4R,5S)-5-(4-amino-6-bromo-5-carbamoyl-1H-pyrrolo[2,3-d]pyrimidine-1-yl)-3,4-dihydroxy-tetrahydrofuran-2-yl)methyl pivalate;

(4) (2S,3R,4S,5S)-2-(4-amino-6-bromo-5-carbamoyl-1H-pyrrolo[2,3-d]pyrimidine-1-yl)-5-(isobutyryloxy methyl)-tetrahydrofuran-3,4-diyl diacetate;

(5) ((2S,3R,4R,5S)-5-(4-amino-6-bromo-5-carbamoyl-1H-pyrrolo[2,3-d]pyrimidine-1-yl)-3,4-dihydroxy-tetrahydrofuran-2-yl)methyl benzoate;

(6) ((2S,3R,4R,5S)-5-(4-amino-6-bromo-5-carbamoyl-1H-pyrrolo[2,3-d]pyrimidine-1-yl)-3,4-dihydroxy-tetrahydrofuran-2-yl)methyl propionate; and (7) ((2S,3R,4R,5S)-5-(4-amino-6-bromo-5-carbamoyl-1H-pyrrolo[2,3-d]pyrimidine-1-yl)-3,4-dihydroxy-tetrahydrofuran-2-yl)methyl cyclohexanecarboxylate.

4. A method for preparing the pyrrolopyrimidine carboxamide derivative of claim 1 comprising the following steps as shown in the following Reaction Scheme 1:

preparing the compound of formula 4 by reacting the compound of formula 2 with the compound of formula 3 in the presence of trimethylsilyl trifluoromethanesulfonate (TMSOTf) after adding N,O-bis(trimethylsilyl) acetamide (BSA) to the compound of formula 2 (step 1);

preparing the compound of formula 5 by adding ammonium hydroxide solution to the compound of formula 4 (step 2); and preparing the compound of formula 1a by adding hydrogen peroxide to the compound of formula 5 (step 3):

[Reaction Scheme 1]

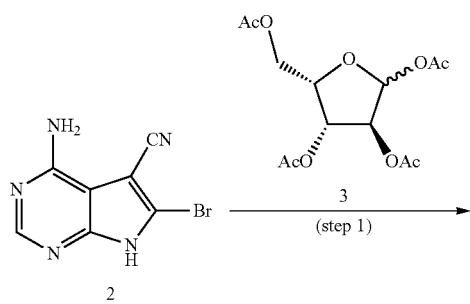

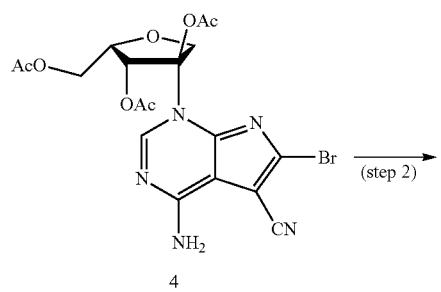

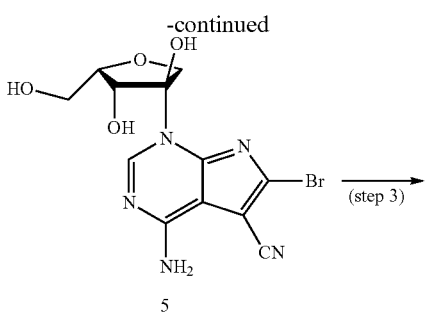

5

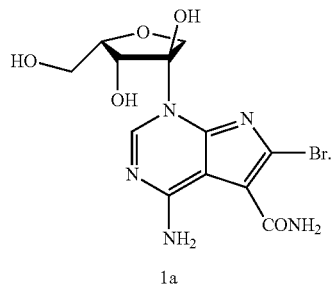

1a

5. The method for preparing the pyrrolopyrimidine carboxamide derivative according to claim 4, further comprising an additional step of preparing the compound of formula 1b' from the compound of formula 1a via esterification as shown in the following Reaction Scheme 2:

[Reaction Scheme 2]

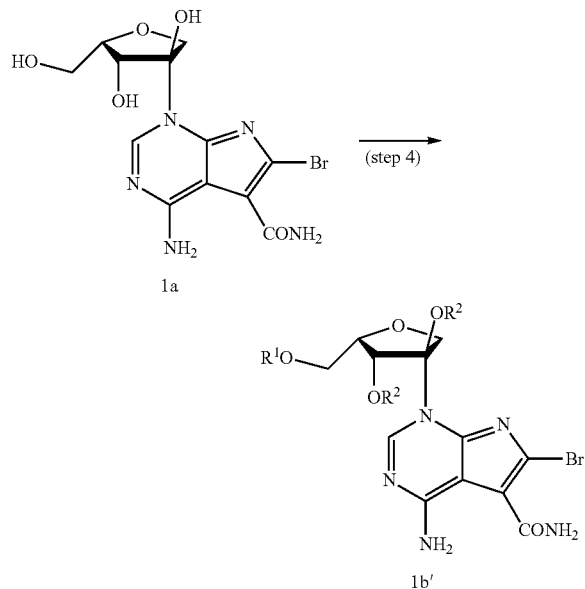

wherein in Reaction Scheme 2,
$R^1$ is $R^3C(=O)$; and
$R^3$ is $C_1$-$C_6$ straight or branched alkyl, $C_3$-$C_8$ cycloalkyl or phenyl; and wherein 1a is contacted with a carboxylic acid anhydride.

6. The method for preparing the pyrrolopyrimidine carboxamide derivative according to claim 4, further comprising wherein the compound of formula 2, which is the starting material, is prepared by the following steps as shown in the following Reaction Scheme 3:

preparing the compound of formula 7 by adding hydrogen bromide to the compound of formula 6, tetracyanoethylene, in the presence of acetone and ethylacetate (step 1); and preparing the compound of formula 2 by adding triethyl orthoformate and ammonia water to the compound of formula 7 (step 2):

[Reaction Scheme 3]

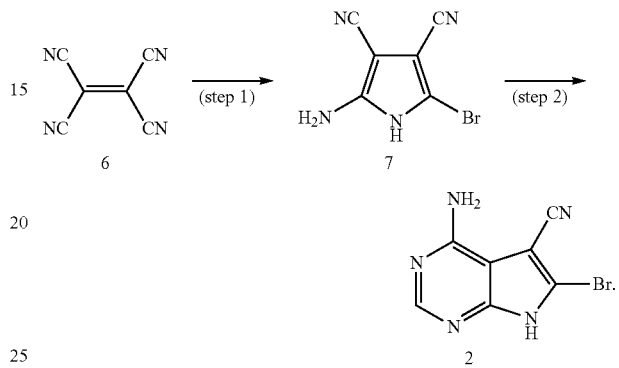

7. The method for preparing the pyrrolopyrimidine carboxamide derivative according to claim 4, further comprising wherein the compound of formula 3 is prepared according to Reaction Scheme 4 by reacting L-xylose of formula 8 with boric acid, to which acetic acid and acetic anhydride are added, followed by reaction at high temperature:

[Reaction Scheme 4]

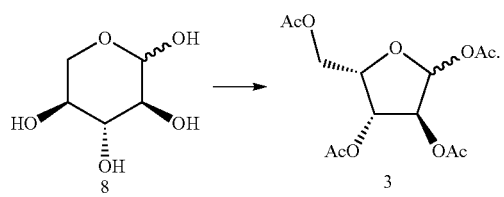

8. The method for preparing the pyrrolopyrimidine carboxamide derivative according to claim 5, further comprising an additional step of preparing the compound of formula 1d from the compound of formula 1b' via esterification as shown in the following Reaction Scheme 5:

[Reaction Scheme 5]

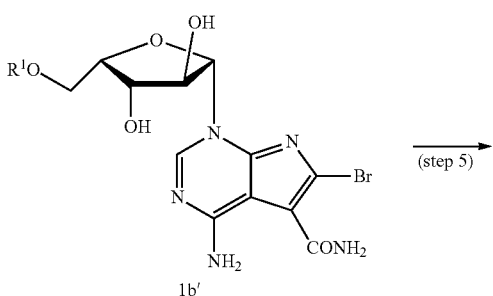

1b'

-continued

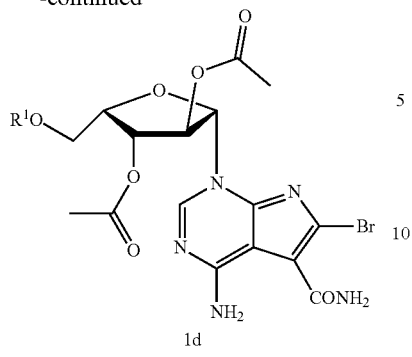
1d wherein in Reaction Scheme 5,
R$^1$ is R$^3$C(=O); and
R$^3$ is C$_1$-C$_6$ straight or branched alkyl, C$_3$-C$_8$ cycloalkyl or phenyl.

9. A method for treating hepatocellular carcinoma comprising administering a therapeutically effective dose of a pyrrolopyrimidine carboxamide derivative or a pharmaceutically acceptable salt thereof of claim 1 to a subject having hepatocellular carcinoma.

10. The method for treating hepatocellular carcinoma according to claim 9, wherein a pyrrolopyrimidine carboxamide derivative or a pharmaceutically acceptable salt thereof has cyclin-dependent kinase (CdK) inhibiting activity.

11. The method for treating hepatocellular carcinoma according to claim 10, wherein the said Cdk includes Cdk1, Cdk2, Cdk7, and Cdk9.

* * * * *

SEQUENCE LISTING

<160> NUMBER OF SEQ ID NOS: 8

<210> SEQ ID NO 1
<211> LENGTH: 20
<212> TYPE: DNA

```
<213> ORGANISM: Artificial Sequence
<220> FEATURE:
<223> OTHER INFORMATION: Synthetic oligonucleotide primer - Mcl-1
      forward

<400> SEQUENCE: 1
cggtaatcgg actcaacctc                                              20

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide primer - Mcl-1
      reverse

<400> SEQUENCE: 2
cctccttctc cgtagccaa                                               19

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide primer - XIAP forward

<400> SEQUENCE: 3
agtggtagtc ctgtttcagc atca                                         24

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide primer - XIAP reverse

<400> SEQUENCE: 4
ccgcacggta tctccttca                                               19

<210> SEQ ID NO 5
<211> LENGTH: 17
<212> TYPE: DNA
<213> ORGANISM: Artificial Sequence
<220> FEATURE:
<223> OTHER INFORMATION: Synthetic oligonucleotide primer - survivin
      forward

<400> SEQUENCE: 5
tgcctggcag ccctttc                                                 17

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide primer - survivin
      reverse

<400> SEQUENCE: 6
cctccaagaa gggccagttc                                              20

<210> SEQ ID NO 7
<211> LENGTH: 18
<212> TYPE: DNA
<213> ORGANISM: Artificial Sequence
<220> FEATURE:
<223> OTHER INFORMATION: Synthetic oligonucleotide primer - GAPDH
```

```
                                    -continued
    forward

<400> SEQUENCE: 7
gaaggtgaag gtcggagt                                                 18

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide primer - GAPDH
      reverse primer

<400> SEQUENCE: 8
gaagatggtg atgggatttc                                               20
```